(12) United States Patent
Ekwuribe et al.

(10) Patent No.: US 8,048,924 B2
(45) Date of Patent: *Nov. 1, 2011

(54) METHODS AND COMPOSITIONS EMPLOYING 4-AMINOPHENYLACETIC ACID COMPOUNDS

(75) Inventors: Nnochiri N. Ekwuribe, Cary, NC (US); Rodger Liddle, Durham, NC (US)

(73) Assignee: Biocon Limited (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/594,046

(22) PCT Filed: Mar. 22, 2005

(86) PCT No.: PCT/US2005/009325
§ 371 (c)(1),
(2), (4) Date: Sep. 25, 2006

(87) PCT Pub. No.: WO2005/094448
PCT Pub. Date: Oct. 13, 2005

(65) Prior Publication Data
US 2007/0060552 A1  Mar. 15, 2007

Related U.S. Application Data

(60) Continuation-in-part of application No. 11/144,093, filed on Jun. 3, 2005, which is a continuation of application No. 10/444,668, filed on May 23, 2003, now Pat. No. 6,903,082, which is a division of application No. 09/942,464, filed on Aug. 29, 2001.

(60) Provisional application No. 60/555,551, filed on Mar. 23, 2004.

(51) Int. Cl.
*A61K 31/196* (2006.01)
(52) U.S. Cl. ...................................... 514/566
(58) Field of Classification Search ........................ None
See application file for complete search history.

(56) References Cited

U.S. PATENT DOCUMENTS

| | | | |
|---|---|---|---|
| 1,157,169 A | 10/1915 | Mettler | |
| 2,270,676 A | 1/1942 | Behnisch et al. | |
| 2,314,023 A | 3/1943 | Straub et al. | |
| 2,336,275 A | 12/1943 | McNally et al. | |
| 2,396,019 A | 3/1946 | Murray | |
| 3,244,694 A | 4/1966 | May et al. | |
| 3,641,040 A | 2/1972 | Carney et al. | |
| 3,915,951 A | 10/1975 | Agback et al. | |
| 4,189,607 A | 2/1980 | Amano et al. | |
| 4,298,595 A | 11/1981 | Parkinson et al. | |
| 4,348,399 A | 9/1982 | Shepherd | |
| 4,374,932 A | 2/1983 | Pitzele et al. | |
| 4,412,992 A | 11/1983 | Chan | |
| 4,455,305 A | 6/1984 | Rokos | |
| 4,472,433 A | 9/1984 | Ueda et al. | |
| 4,493,823 A | 1/1985 | Moller et al. | |
| 4,496,553 A | 1/1985 | Halskov | |
| 4,504,494 A | 3/1985 | Grollier et al. | |
| 4,528,367 A | 7/1985 | Agback et al. | |
| 4,539,198 A | 9/1985 | Powell et al. | |
| 4,540,685 A | 9/1985 | Bauer | |
| 4,559,330 A | 12/1985 | Agback et al. | |
| 4,591,584 A | 5/1986 | Agback | |
| 4,595,699 A | 6/1986 | Terada et al. | |
| 4,628,083 A | 12/1986 | Agback | |
| 4,632,921 A | 12/1986 | Bauer | |
| 4,657,900 A | 4/1987 | Powell et al. | |
| 4,663,308 A | 5/1987 | Saffran et al. | |
| 4,664,256 A | 5/1987 | Halskov | |
| 4,670,112 A | 6/1987 | Lund | |
| 4,699,902 A | 10/1987 | Bauer | |
| 4,720,506 A | 1/1988 | Munakata et al. | |
| 4,725,676 A | 2/1988 | Agback et al. | |
| 4,737,240 A | 4/1988 | Davis et al. | |
| 4,780,318 A | 10/1988 | Appelgren et al. | |
| 4,788,331 A | 11/1988 | Sjöstrand | |
| 4,837,229 A | 6/1989 | Rokos et al. | |
| 4,849,416 A | 7/1989 | Pendleton et al. | |
| 4,873,321 A | 10/1989 | Omura et al. | |
| 4,880,794 A | 11/1989 | Halskov | |
| 4,889,846 A | 12/1989 | Crossley | |
| 4,904,765 A | 2/1990 | Derber et al. | |
| 4,911,922 A | 3/1990 | Masuhara et al. | |
| 4,920,206 A | 4/1990 | Behringer et al. | |
| RE33,239 E | 6/1990 | Halskov | |
| 4,933,330 A | 6/1990 | Jorgensen et al. | |
| 4,960,765 A | 10/1990 | Halskov | |
| 4,999,347 A | 3/1991 | Sorenson | |

(Continued)

FOREIGN PATENT DOCUMENTS

DE       4121849 A1       1/1993

(Continued)

OTHER PUBLICATIONS

The Merck Manual, 17th edition (1999), pp. 307-311.*
Database Crossfire Beilstein Online; Bellstein Institut Zur Foerderung Der Chemischen Wissenschaften, Frankfurt, AM Main, De; Database-Accession No. 926638 (BRN), XP002192315 & Journal of Organic Chemistry, vol. 55, No. 17, 1990, pp. 5165-5170; Easton, US.
Tse-Tsing Chu et al.; A Proof of the Unsymmetrical Structure of the Azoxy Group; Journal of the American Chemical Society; 1993; pp. 2841-2850; 55; USA.
Par E. Frommel et al.; La paraminobenzolsulfonesuccinylimide, sulfamide soluble neutre et injectable; Holv. Physiol. Acta; 1945; pp. 261-268; 3.
E. Hackmann et al.; Nuovi Azoderivatl Solfammidici; Boll. Chim. Farm.; 1975; pp. 501-508; 114.

(Continued)

*Primary Examiner* — Phyllis G. Spivack
(74) *Attorney, Agent, or Firm* — Marianne Fuierer; Moore & Van Allen, PLLC

(57) ABSTRACT

The invention provides compositions comprising 4-APAA compounds and methods for treating disorders involving inflammation of the intestinal system, such as inflammatory bowel disease. The methods and compositions of the invention also include combinations of 4-APAA compounds and 5-ASA compounds for treatment of such disorders.

13 Claims, 22 Drawing Sheets

U.S. PATENT DOCUMENTS

| | | | |
|---|---|---|---|
| 5,010,069 A | 4/1991 | Bottom et al. | |
| 5,013,727 A | 5/1991 | Halskov | |
| 5,026,560 A | 6/1991 | Makino et al. | |
| 5,037,968 A | 8/1991 | Simon et al. | |
| 5,041,431 A | 8/1991 | Halskov | |
| 5,082,651 A | 1/1992 | Healey et al. | |
| 5,089,468 A | 2/1992 | Yoshida et al. | |
| 5,137,916 A | 8/1992 | Ulrich et al. | |
| 5,244,922 A | 9/1993 | Burzynski | |
| 5,254,587 A | 10/1993 | Burzynski | |
| 5,272,176 A | 12/1993 | Ulrich et al. | |
| 5,274,002 A | 12/1993 | Hawkins | |
| 5,330,981 A | 7/1994 | Rosini et al. | |
| 5,352,681 A | 10/1994 | Wittebrood et al. | |
| 5,378,470 A | 1/1995 | Lahr | |
| 5,391,575 A | 2/1995 | Burzynski | |
| 5,393,779 A | 2/1995 | Holloway et al. | |
| 5,409,711 A | 4/1995 | Mapelli et al. | |
| 5,434,184 A | 7/1995 | Holloway et al. | |
| 5,476,849 A | 12/1995 | Ulrich et al. | |
| 5,480,910 A | 1/1996 | Holloway et al. | |
| 5,484,605 A | 1/1996 | Scheiffele et al. | |
| 5,487,770 A | 1/1996 | Dyllick-Brenzinger et al. | |
| 5,498,608 A | 3/1996 | Johnson et al. | |
| 5,502,078 A | 3/1996 | Holloway et al. | |
| 5,514,676 A | 5/1996 | Ulrich et al. | |
| 5,519,014 A | 5/1996 | Borody | |
| 5,541,170 A | 7/1996 | Rhodes et al. | |
| 5,541,171 A | 7/1996 | Rhodes et al. | |
| 5,574,050 A | 11/1996 | Carrell et al. | |
| 5,593,971 A | 1/1997 | Tschollar et al. | |
| 5,602,183 A | 2/1997 | Martin et al. | |
| 5,629,012 A | 5/1997 | Halskov | |
| 5,629,020 A | 5/1997 | Leone-Bay et al. | |
| 5,631,294 A | 5/1997 | Kurtz et al. | |
| 5,635,533 A | 6/1997 | Samid | |
| 5,637,618 A | 6/1997 | Kurtz et al. | |
| 5,646,182 A | 7/1997 | Burzynski | |
| 5,648,380 A | 7/1997 | Martin | |
| 5,654,333 A | 8/1997 | Samid | |
| 5,661,179 A | 8/1997 | Samid | |
| 5,663,208 A | 9/1997 | Martin | |
| 5,667,789 A | 9/1997 | Collin et al. | |
| 5,668,123 A | 9/1997 | Berry | |
| 5,674,912 A | 10/1997 | Martin | |
| 5,696,243 A | 12/1997 | Beckmann et al. | |
| 5,703,073 A | 12/1997 | Garvey et al. | |
| 5,708,025 A | 1/1998 | Samid | |
| 5,716,648 A | 2/1998 | Halskov et al. | |
| 5,725,872 A | 3/1998 | Stamm et al. | |
| 5,731,302 A | 3/1998 | Farolfi et al. | |
| 5,739,299 A | 4/1998 | Hall | |
| 5,747,477 A | 5/1998 | Carceller et al. | |
| 5,747,532 A | 5/1998 | Lai | |
| 5,770,708 A | 6/1998 | Bermes | |
| 5,817,321 A | 10/1998 | Alakhov et al. | |
| 5,827,332 A | 10/1998 | Zeidler et al. | |
| 5,840,724 A | 11/1998 | Fenton et al. | |
| 5,840,966 A | 11/1998 | Kumarathasan et al. | |
| 5,843,994 A | 12/1998 | Samid | |
| 5,852,056 A | 12/1998 | Samid | |
| 5,861,426 A | 1/1999 | Del Soldato et al. | |
| 5,866,608 A | 2/1999 | Kurtz et al. | |
| 5,874,479 A | 2/1999 | Martin | |
| 5,877,213 A | 3/1999 | Samid | |
| 5,883,124 A | 3/1999 | Samid | |
| 5,905,073 A | 5/1999 | Johnson et al. | |
| 5,935,601 A | 8/1999 | Leone-Bay et al. | |
| 5,939,455 A | 8/1999 | Rephaeli | |
| 5,939,456 A | 8/1999 | Perrine | |
| 5,945,411 A | 8/1999 | Larson et al. | |
| 5,955,472 A | 9/1999 | Hays et al. | |
| 5,962,710 A | 10/1999 | Gschneidner et al. | |
| 5,973,126 A | 10/1999 | Ueno et al. | |
| 5,985,927 A | 11/1999 | Kreutz | |
| 6,008,208 A | 12/1999 | Petrie et al. | |
| 6,008,250 A | 12/1999 | Kurtz et al. | |
| 6,037,376 A | 3/2000 | Samid | |
| 6,043,233 A | 3/2000 | Garvey et al. | |
| 6,124,504 A | 9/2000 | Hupperts et al. | |
| 6,127,349 A | 10/2000 | Chasalow | |
| 6,166,044 A * | 12/2000 | Sandborn et al. | 514/343 |
| 6,183,549 B1 | 2/2001 | Wight | |
| 6,191,265 B1 | 2/2001 | Hamprecht | |
| 6,197,341 B1 | 3/2001 | Friess et al. | |
| 6,225,296 B1 | 5/2001 | Kapadia | |
| 6,245,735 B1 | 6/2001 | Pier | |
| 6,245,802 B1 | 6/2001 | Iyengar et al. | |
| 6,277,412 B1 | 8/2001 | Otterbeck | |
| 6,277,836 B1 | 8/2001 | Borody | |
| 6,281,203 B1 | 8/2001 | Touzan et al. | |
| 6,294,186 B1 | 9/2001 | Beerse et al. | |
| 6,313,107 B1 | 11/2001 | Vasudevan et al. | |
| 6,319,951 B1 | 11/2001 | Chege | |
| 6,326,364 B1 | 12/2001 | Lin et al. | |
| 6,344,561 B2 | 2/2002 | Vuligonda | |
| 6,348,497 B1 | 2/2002 | Billingham | |
| 6,369,261 B1 | 4/2002 | Johnson et al. | |
| 6,375,733 B1 | 4/2002 | Bindra | |
| 6,380,256 B1 | 4/2002 | Vasudevan et al. | |
| 6,383,471 B1 | 5/2002 | Chen et al. | |
| 6,384,023 B2 | 5/2002 | Singleton | |
| 6,387,892 B1 | 5/2002 | Vasudevan et al. | |
| 6,387,952 B1 | 5/2002 | Mazurek et al. | |
| 6,391,832 B2 | 5/2002 | Lyons et al. | |
| 6,399,647 B2 | 6/2002 | Kaigutkar et al. | |
| 6,403,646 B1 | 6/2002 | Perlmutter et al. | |
| 6,409,812 B1 | 6/2002 | Ueno et al. | |
| 6,413,494 B1 | 7/2002 | Lee et al. | |
| 6,414,026 B1 | 7/2002 | Billingham | |
| 6,423,696 B1 | 7/2002 | Collins et al. | |
| 6,426,338 B1 | 7/2002 | Borody | |
| 6,437,104 B1 | 8/2002 | Nickel et al. | |
| 6,444,221 B1 | 9/2002 | Shapiro | |
| 6,458,776 B1 | 10/2002 | Ekwuribe et al. | |
| 6,479,528 B1 | 11/2002 | Kuret et al. | |
| 6,488,947 B1 | 12/2002 | Bekele | |
| 6,495,552 B2 | 12/2002 | Vasudevan et al. | |
| 6,528,076 B2 | 3/2003 | Small et al. | |
| 6,541,670 B2 | 4/2003 | Ottosen | |
| 6,551,620 B2 | 4/2003 | Otterbeck et al. | |
| 6,551,632 B2 | 4/2003 | Borody | |
| 6,552,077 B2 | 4/2003 | Cohen | |
| 6,566,507 B2 | 5/2003 | Wood et al. | |
| 6,573,252 B1 | 6/2003 | Del Soldato | |
| 6,583,128 B2 * | 6/2003 | Ekwuribe et al. | 514/150 |
| 6,583,273 B1 | 6/2003 | Bacher et al. | |
| 6,589,944 B1 | 7/2003 | Rahbar | |
| 6,599,748 B1 | 7/2003 | Nakajima et al. | |
| 6,602,987 B1 | 8/2003 | Wilchek et al. | |
| 6,613,807 B2 | 9/2003 | Uhrich | |
| 6,630,463 B2 | 10/2003 | Kikuchi et al. | |
| 6,653,352 B2 | 11/2003 | Barr et al. | |
| 6,660,283 B2 | 12/2003 | Breton et al. | |
| 6,720,344 B2 | 4/2004 | Kerwin et al. | |
| 6,727,235 B2 | 4/2004 | Kreutz | |
| 6,791,788 B2 | 9/2004 | Gustafson et al. | |
| 6,808,616 B2 | 10/2004 | Sanchez-Cano | |
| 6,809,087 B2 | 10/2004 | Carceller et al. | |
| 6,824,786 B2 | 11/2004 | Yu et al. | |
| 6,867,233 B2 | 3/2005 | Roselle et al. | |
| 6,881,553 B2 | 4/2005 | Kabbash et al. | |
| 6,884,808 B2 | 4/2005 | Kikuchi et al. | |
| 6,887,632 B2 | 5/2005 | Saminathan et al. | |
| 6,903,082 B2 * | 6/2005 | Ekwuribe et al. | 514/162 |
| 6,907,736 B2 | 6/2005 | Ohnishi et al. | |
| 6,919,325 B2 | 7/2005 | Linz et al. | |
| 6,943,192 B2 | 9/2005 | Burzynski | |
| 6,949,555 B2 | 9/2005 | Guitard et al. | |
| 7,022,333 B2 | 4/2006 | Syverson et al. | |
| 7,030,146 B2 | 4/2006 | Baynes et al. | |
| 7,053,071 B2 | 5/2006 | Dawson et al. | |
| 7,064,185 B2 | 6/2006 | Lau | |
| 7,119,119 B2 * | 10/2006 | Ekwuribe et al. | 514/567 |
| 7,151,095 B2 | 12/2006 | Ekwuribe et al. | |
| 7,189,518 B2 | 3/2007 | Schönbeck et al. | |
| 7,238,680 B2 | 7/2007 | Rosen | |

| | | |
|---|---|---|
| 7,265,153 B2 | 9/2007 | Faller et al. |
| 7,425,578 B2 * | 9/2008 | Ekwuribe et al. ............. 514/613 |
| 2001/0046509 A1 | 11/2001 | Breton et al. |
| 2002/0061339 A1 | 5/2002 | Stogniew et al. |
| 2002/0120008 A1 | 8/2002 | Benzer et al. |
| 2002/0143011 A1 | 10/2002 | Warrellow et al. |
| 2002/0160986 A1 | 10/2002 | Vasudevan et al. |
| 2002/0183285 A1 | 12/2002 | Vasudevan et al. |
| 2003/0013746 A1 | 1/2003 | Hudson et al. |
| 2003/0017995 A1 | 1/2003 | Khalifah et al. |
| 2003/0018077 A1 | 1/2003 | Billingham et al. |
| 2003/0119792 A1 | 6/2003 | Roca |
| 2003/0125306 A1 | 7/2003 | Lan Hargest et al. |
| 2003/0162754 A1 | 8/2003 | Ligon |
| 2003/0171306 A1 | 9/2003 | Davis et al. |
| 2003/0181618 A1 | 9/2003 | Saminathan |
| 2003/0191186 A1 | 10/2003 | Ekwuribe et al. |
| 2005/0090553 A1 | 4/2005 | Shapiro |
| 2008/0033153 A1 | 2/2008 | Riggs-Sauthier et al. |

FOREIGN PATENT DOCUMENTS

| | | |
|---|---|---|
| EP | 0094599 A1 | 11/1983 |
| EP | 0036636 B1 | 2/1984 |
| EP | 0465802 A1 | 1/1992 |
| ES | 8606254 A1 | 5/1985 |
| GB | 2203434 A | 10/1988 |
| WO | WO 94/00135 | 1/1994 |
| WO | WO 95/31194 | 11/1995 |

OTHER PUBLICATIONS

B.C. Jain et al.; Studies in Sulphanilamides. Part XIII Reaction with Dicarboxylic Acids. Some New $N^1$—and $N^4$—Acyl and Heterocyclic Derivatives; J. Indian Chem. Soc.; 1947; pp. 173-176; 24.

Isami Kimura et al.; Determination of the Active Moiety of BX661A, a New Therapeutic Agent for Alcerative Colitis, by Studying Its Therapeutic Effects on Ulcerative Colitis Induced by Dextran Sulfate Sodium in Rats; Drug Res.; 1998; pp. 1091-1098; 48 (II) (11).

S. A. A. Osman et al.; Synthesis of SulfanilamIdo-Naphthoquinones as Potential Antituberculous Agents; Journal of Pharmaceutical Sciences; Jan. 1983; pp. 68-71; vol. 72, No. 1; American Pharmaceutical Association.

Antonio Gómez-Muñoz et al.; 5-Aminosalicylate stimulates phospholipase D activity in macrophages; Biochimica et Biophysica Acta; 2001; pp. 110-118; 1533; Elsevier Science B. V.

Rosalind P. Chan et al.; Studies of Two Novel Sulfasalazine Analogs, Ipsalazide and Balsalazide; Digestive Diseases and Sciences; Jul. 1983; vol. 28, No. 7; Digestive Disease Systems, Inc.

Paul Retgeerts; Strategies in the prevention of post-operative recurrence in Crohn's Disease; Best Practice & Research Clinical Gastroenterology, 2003; pp. 63-73; vol. 17, No. 1; Elsevier Science Ltd.

M.C. Di Paolo et al.; Sulphasalazine and 5-aminosalicylic acid in long-term treatment of ulcerative colitis: report on tolerance and side-effects; Digest Liver Dis.; 2001; pp. 563-569; 33.

E. K. Fields et al.; Diaryl Substituted Maleic Anhydrides; J. Org. Chem.; 1990; pp. 5165-6170; 55; American Chemical Society.

Friedrich Nerdel et al.; Chemical Abstracts; 1961; pp. 443-444; vol. 55.

Frank D. King; Bloisosteres, Conformational Restriction, and Prodrugs—Case History: An Example of a Conformational Restriction Approach; Medicinal Chemistry : Principles and Practice; 1994; pp. 206-225 (pp. 216-217, Table 4); Cambridge, RSC, GB.

Beilstein Search Results, 5522653, 1884.

* cited by examiner

METHODS AND COMPOSITIONS EMPLOYING 4-AMINOPHENYLACETIC ACID COMPOUNDS

CROSS-REFERENCE TO RELATED APPLICATIONS

This application is a National Stage Entry under the provisions of 35 U.S.C. §371 of International Patent Application No. PCT/US2005/009325 filed on Mar. 22, 2005, which in turn claims priority of U.S. Provisional Application No. 60/555,551 filed on Mar. 23, 2004; and is a Continuation-in-Part of U.S. application Ser. No. 11/144,093 filed on Jun. 3, 2005 titled "IMMUNOREGULATORY COMPOUNDS AND DERIVATIVES AND METHODS OF TREATING DISEASES THEREWITH" issued on Oct. 10, 2006 as U.S. Pat. No. 7,119,119, which is a continuation of application Ser. No. 10/444,668, filed on May 23, 2003, now U.S. Pat. No. 6,903,082, which is a divisional of application Ser. No. 09/942,464, filed on Aug. 29, 2001 now U.S. Pat. No. 6,583,128.

FIELD OF THE INVENTION

The present invention relates to methods and compositions employing 4-APAA compounds as monotherapy or in combination therapies for disorders involving inflammation of the digestive system and/or mucosal tissues.

BACKGROUND OF THE INVENTION

A wide variety of bowel diseases are related to the inflammatory processes. Two of the most important inflammatory conditions are ulcerative colitis (UC) and Crohn's disease (CD). UC is a chronic inflammatory condition of the internal lining of the colon. It extends from the rectum and can involve the entire colon. CD can involve the entire gastrointestinal (GI) tract but is usually limited to the small and large intestine. CD can extend through the bowel wall leading to other complications. About 20% of patients with CD have disease isolated to the colon. Both UC and CD are chronic conditions, and treatment typically follows a two-phase treatment approach: induction and then maintenance of remission. UC and CD are characterized by abdominal pain, bloody diarrhea, and bowel wall inflammation. For many patients, the disease is episodic, occurring as a cycle of flares and remissions with considerable morbidity. Symptoms can be mild or very severe and disabling. They can develop gradually or have a sudden onset.

Approximately one million Americans suffer with either UC or CD. In Western Europe and the United States the prevalence of UC is 70 to 150 per 100,000 while the prevalence of CD is 40 to 100 per 100,000. These diseases can affect persons of any age, but are more common in the second and third decades. Males and females are equally affected. Risk of disease is higher in some ethnic groups than others. Overall, the incidence of UC appears to be stabilizing, but the incidence of CD is increasing, especially among young people.

The causes of UC and CD are unknown, although genetic predisposition, infectious bacterial and viral agents, as well as environmental factors are suspected to play a role. Recent experimental and clinical studies suggest that the initiation and pathogenesis of CD and UC are multifactorial, involving interactions among genetic, environmental, and immune factors. Regardless of exactly how these interactions ultimately promote chronic gut inflammation, it is becoming increasingly apparent that the immune system plays a critical role in disease pathogenesis.

Current therapies for inflammatory bowel diseases fall into 4 classes: 1) corticosteroids 2) aminosalicylates, 3) immunomodulators and 4) antibiotics. Aminosalicylate drugs such as sulfasalazine or mesalamine are the mainstay of treatment for mild to moderate disease. Immunomodulatory agents such as azathioprine and 6-mercaptopurine are used as steroid-sparing agents but have a variety of adverse side effects, often precluding use in many patients. Additional immunomodulators such as monoclonal antibodies against tumor necrosis factor α (anti-TNFα) are effective in some patients with Crohn's disease.

Following introduction into clinical medicine for the treatment of rheumatoid arthritis 40 years ago, aminosalicylates (e.g., 5-ASA) have become the primary treatment for ulcerative colitis (UC). Aminosalicylates (e.g., 5-ASA) are first-line inductive agents for the treatment of mildly to moderately active disease, as well as the primary maintenance therapy for remitted UC, and are used in conjunction with corticosteroids during the transition from inductive to maintenance therapy.

Sulfasalazine was the original prototype aminosalicylate and was designed with the concept of combining an anti-bacterial agent (sulfapyridine) and an anti-inflammatory agent (5-ASA):

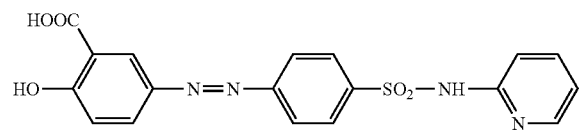

Although the mode of action of sulfasalazine is not clearly understood, multiple clinical studies indicate that the major therapeutic action resides in the 5-ASA moiety. The primary limitation of sulfasalazine is the significant rate of adverse events related to the sulfapyridine moiety, thereby compromising the clinical usefulness of sulfasalazine. As many as 30 to 40 percent of patients are unable to tolerate the doses required to provide optimal treatment benefits.

Commercially available products (mesalamine, ASA-COL®, PENTASA®, ROWASA®) use various means of delivering 5-ASA to inflamed intestinal mucosa. All of these compounds deliver 5-ASA without the sulfapyridine component of sulfasalazine that causes most of the adverse reactions.

Olsalazine, having the following formula, has been used to treat ulcerative colitis.

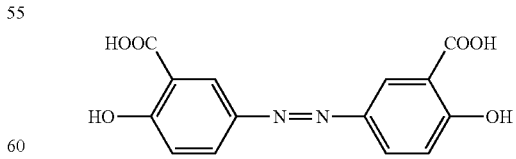

In addition to being relatively expensive to make, olsalazine can have adverse side effects, including diarrhea.

It is known to use azathioprine (6-(1-methyl-4-nitroimidazol-5-ylthio)purine) in the treatment of inflammatory bowel disease. Azathioprine has the following chemical structure:

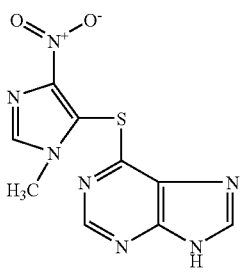

It is also known to use 6-mercaptopurine, a metabolite of azathioprine, to treat inflammatory bowel disease. 6-mercaptopurine has the following chemical structure:

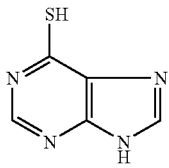

Methotrexate (L-4-amino-$N^{10}$-methylpteroyl-glutamic acid) has also been used to treat inflammatory bowel disease. Methotrexate has the following chemical structure:

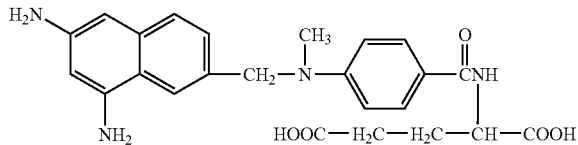

Actarit (4-acetylaminophenylacetic acid) is an immunomodulatory drug that was approved in Japan in 1994 for use in the treatment of rheumatoid arthritis. Four-aininophenylacetic acid (4-APAA) is a precursor to actarit and in vivo studies demonstrate that 4-APAA undergoes acetylation to form actarit. Both actarit and 4-APAA possess immunomodulatory activity.

The polypeptide cyclosporine, which has traditionally been given to transplant patients to prevent organ rejection, has also been used to treat inflammatory bowel disease. The use of cyclosporine to treat IBD can be limited, however, by the various side effects associated with this medication. These side effects include high blood pressure, kidney damage, tremors, headaches, seizures, excessive hair growth, excessive gum growth, confusion, coma, and gout.

after a 30 minute pretreatment with 5-ASA. (A) Pretreatment with 0.01 µg 5-ASA. (B) Pretreatment with 0.1 µg 5-ASA (C) Pretreatment with 1.0 µg 5-ASA. (D) Pretreatment with 10 µg 5-ASA. Scale bar=100 µm.

Figure 20:
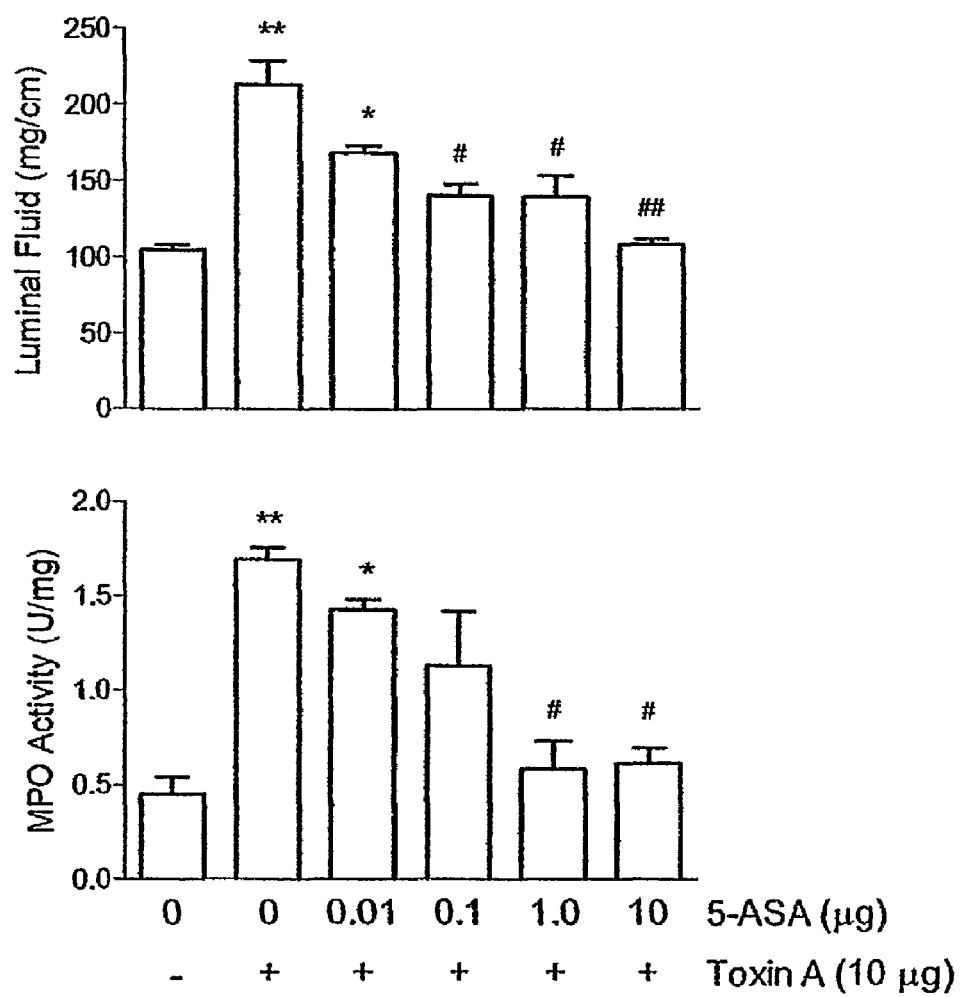

FIG. 20 shows the effects of four doses of 5-ASA on toxin A-induced (10 µg) colonic luminal fluid accumulation and MPO activity. Toxin A significantly stimulated luminal fluid accumulation and MPO activity and toxin A-induced luminal fluid accumulation was significantly inhibited by 5-ASA treatment at the three highest doses tested. Toxin A-induced MPO activity was significantly inhibited by 5-ASA treatment only at the 1.0 and 10 µg 5-ASA doses but not at the 5-ASA doses of 0.01 and 0.1 µg. The values shown are mean±SEM; N=3. *$P<0.01$ vs. toxin $A^-$/5-ASA 0; **$P<0.001$ vs. toxin $A^-$/5-ASA 0; $^\#$ $P<0.01$ vs. toxin $A^+$/5-ASA 0; $^{\#\#\#}$ $P<0.001$ vs. toxin $A^+$/5-ASA 0.

Figure 21:
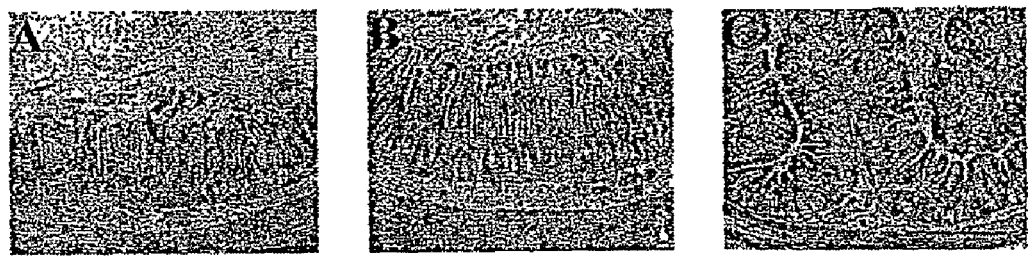

FIGS. 21 A-C show the effects of toxin A on colon histology and inhibition of these effects by treatment with 4-APAA, 5-ASA, and a combination of 4-APAA and 5-ASA. H&E-stained sections of rat colon were prepared after the rats were treated for three hours with toxin A (10 µg) after a 30 minute pretreatment with 4-APAA, 5-ASA, or both. (A) Pretreatment with 10 ng 4-APAA. (B) Pretreatment with 10 ng 5-ASA. (C) Pretreatment with 10 ng 4-APAA plus 10 ng 5-ASA. Scale bar=100 µm.

Figure 22:
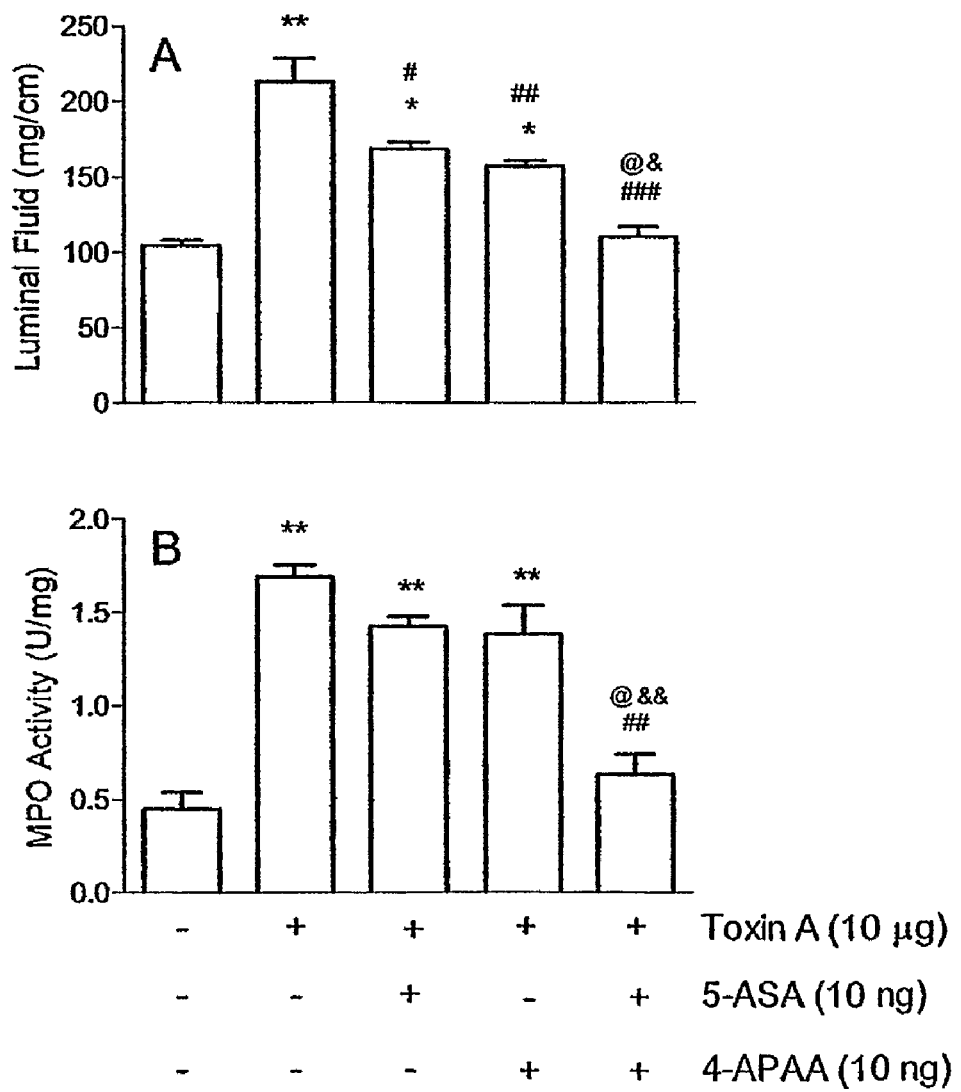

FIGS. 22 A-B show the effects of low doses of 4-APAA, 5-ASA, and both compounds on toxin A-induced (10 µg) colonic luminal fluid accumulation and MPO activity. Toxin A significantly stimulated luminal fluid accumulation and MPO activity and this was significantly inhibited by both compounds individually and by the combination of both compounds. However, the combination of both compounds inhibited significantly more toxin A-induced luminal fluid accumulation than either compound alone. Toxin A-induced MPO activity was significantly inhibited only by the combination of both 4-APAA and 5-ASA. The values shown are mean±SEM; N=3. *$P<0.01$ vs. toxin $A^-$/4-APAA$^-$/5-ASA$^-$; **$P<0.001$ vs. toxin $A^-$/4-APAA$^-$/5-ASA$^-$; $^\#$ $P<0.05$ vs. toxin $A^+$; $^{\#\#}$ $P<0.01$ vs. toxin $A^+$; $^{\#\#\#\#}$ $P<0.001$ vs. toxin $A^+$; $^@$ $P<0.01$ vs. toxin $A^{30}$/5-ASA$^+$; $^\&$ $P<0.05$ vs. toxin $A^+$/4-APAA$^+$; $^{\&\&}$ $P<0.01$ vs. toxin $A^+$/4-APAA$^+$.

DETAILED DESCRIPTION OF THE INVENTION

The invention provides methods and compositions making use of 4-APAA compounds as monotherapy or in combination therapies for disorders involving inflammation of the digestive system or mucosal tissues.

The terminology used in the description of the invention is for the purpose of describing particular embodiments only and is not intended to be limiting of the invention. As used herein, the following terms have the meanings indicated:

The singular forms "a," "an," and "the" are intended to include the plural forms as well, unless the context clearly indicates otherwise.

The term "related compounds" includes analogs, derivatives, and compounds comprising the basic structural features that are responsible for the compound's therapeutic activity.

The term "digestive system" as used herein is broadly defined as the organs that are responsible for getting food into and out of the body and for making use of food to keep the body healthy, including the mouth, esophagus, stomach, liver, gallbladder, pancreas, small intestine, colon, and rectum.

"Between" should be interpreted to include the end-points. The term "up to" should be interpreted to include the upper limit.

"Effective amount" refers to an amount of a compound or composition that is sufficient to produce a desired effect, which can be a therapeutic effect. The effective amount will vary with the age, general condition of the subject, the severity of the condition being treated, the particular biologically active agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000).

"Hydrolyzable" refers to bonds that are hydrolyzed under physiological conditions.

"Solubility" refers to the tendency of one substance to blend uniformly with another.

"Chemical stability" refers to the stability of a given compound in physiological environments. For example, chemical stability refers to the stability of the biologically active agent or prodrug in environments characterized by conditions such as, but not limited to, the presence of plasma, the presence of proteases, the presence of liver homogenate, the presence of acidic conditions, and the presence of basic conditions.

A "pharmaceutically acceptable" component such as a salt, carrier, excipient or diluent of a composition according to the present invention is a component that (i) is compatible with the other ingredients of the composition in that it can be combined with the prodrugs of the present invention without rendering the prodrug unsuitable for its intended purpose, and (ii) is suitable for use with subjects as provided herein without undue adverse side effects (such as toxicity, irritation, and allergic response). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents.

"Pharmaceutically acceptable salts" are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, talmic acid, palmitic acid, alginic acid, polyglutamic acid, naphthalenesulfonic acid, methanesulfonic acid, p-toluenesulfonic acid, naplithalenedisulfonic acid, polygalacturonic acid, and the like; and (b) salts formed from elemental anions such as chlorine, bromine, and iodine.

The term "therapeutic agent," as used herein to describe a compound, is intended to cover various forms of the compound, including its esters and pharmaceutically acceptable salts.

"Functional derivative" is used to describe a derivative of a parent compound that has the same or substantially similar pharmacological activity as the parent compound.

"Treat" or "treating" refers to any type of treatment that imparts a modulating effect, which, for example, can be a beneficial effect to a subject afflicted with a disorder, disease or illness, including improvement in the condition of the subject (e.g., in one or more symptoms), delay in the progression of the condition, and/or prevention or delay of the onset of the disorder, change in clinical parameters, disease or illness, etc.

"Inflammatory bowel disease" includes ulcerative colitis and Crohn's disease.

"Non-absorbable antibiotic" means a compound having anti-bacterial activity, which, when delivered orally, results in less than 2 percent of the compound being excreted in the urine of the subject.

The term "4-APAA compounds" as used herein is broadly defined to include 4-aminophenylacetic acid and related compounds and compounds that react under physiological conditions to form or release 4-aminophenylacetic acid and related compounds, having efficacy in the treatment of inflammatory conditions of the digestive system or mucosal tissues, such as inflammatory bowel conditions. The abbreviation "4-aceAPAA" refers to acetylated 4-APAA.

The term "5-ASA compounds" as used herein is broadly defined to include 5-aminosalicylic acid and related compounds and compounds that react under physiological conditions to form or release 5-aminosalicylic acid and related compounds, having efficacy in the treatment of inflammatory conditions of the digestive system or mucosal tissues, such as inflammatory bowel conditions. The abbreviation "5-aceASA" refers to acetylated 5-ASA.

4-APAA Compounds

In one embodiment, the invention makes use of 4-APAA compounds in the treatment of bowel conditions. One class of 4-APAA compounds useful in the invention includes 4-APAA compounds that are not azo bonded to a carrier molecule. Examples of such non-azo bonded 4-APAA compounds include:

(4-aminophenyl)-acetic acid:

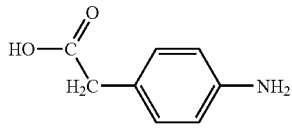

(4-acetylamino-phenyl)-acetic acid:

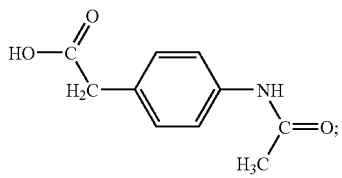

4-aminophenylacetic acid derivatives, such as:

(Formula I)

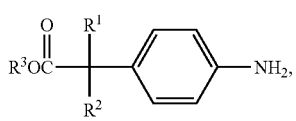

$R^1$, $R^2$, and $R^3$ are independently hydrogen or $C_1$ to $C_4$ alkyl.

Another class of 4-APAA compounds useful in the invention includes 4-APAA compounds that are azo bonded to a carrier molecule. Examples of such azo bonded 4-APAA compounds include:

the 4-aminophenylacetic acid azo-bonded dimer, [4-(4-Carboxymethyl-phenylazo)-phenyl]-acetic acid:

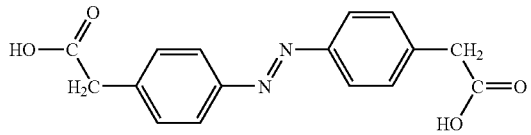

4-aminophenylacetic acid coupled to a 5-ASA compound or coupled to a 4-aminophenylacetic acid derivative, such as diazo bonded compounds having the following formula:

(Formula II)

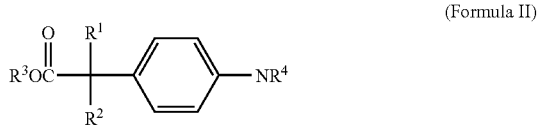

where $R^1$, $R^2$, and $R^3$ are independently hydrogen or $C_1$ to $C_4$ alkyl, and $R^4$ is:

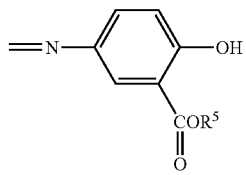

where $R^5$ is selected from the group consisting of hydrogen and $C_1$ to $C_4$ alkyl, or

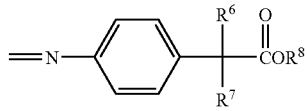

where $R^6$, $R^7$ and $R^8$ are independently hydrogen or $C_1$ to $C_4$ alkyl. As with all of the therapeutic agents described herein, the invention includes the esters or pharmaceutically acceptable salts of the compounds of Formula II.

A particularly preferred 4-APAA compound is the APAZA™ compound (Nobex Corp., Durham N.C.), 5-(4-carboxymethyl-phenylazo)-2-hydroxy-benzoic acid:

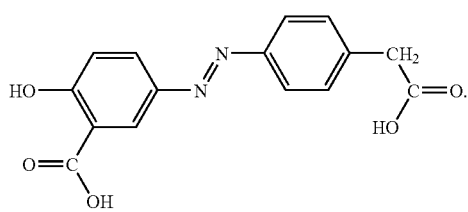

In some embodiments, the invention employs a 4-APAA compound but excludes the APAZA™ compound and/or excludes the compounds of Formula II above wherein $R^4$ is

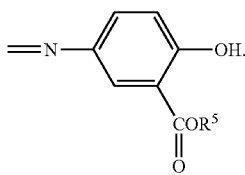

The carrier molecule can be active or inactive. Carrier molecules generally include a core phenylamine moiety:

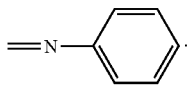

Preferred inactive carrier molecules are those exhibiting little or no toxicity; however, it will be appreciated that the degree of toxicity permitted must be balanced against the benefit of the drug. In one embodiment, the carrier molecules are chosen such that they are not readily absorbed into the bloodstream after cleavage of the azo bond in the intestine, so that a substantial amount of the carrier molecule leaves the body with the feces. It will be appreciated that a wide range of known structures can be employed as carrier molecules.

As discussed in more detail below, in some embodiments, the compositions and methods of the invention employ both a 4-APAA compound that is azo bonded to a carrier molecule and a 4-APAA compound that is not azo-bonded to a carrier molecule.

4-APAA Compounds and 5-ASA Compounds

The invention makes use of combination therapies employing 4-APAA compounds and 5-ASA compounds in the treatment of disorders involving inflammation of the digestive system or mucosal tissues, such as inflammatory bowel conditions. As demonstrated in the examples set forth herein, this combination can be synergistic relative to either of the components alone. In some cases, the combination of 4-APAA compounds with 5-ASA compounds can be additive.

One class of 5-ASA compounds useful in the invention include 5-ASA compounds that are not azo bonded to a carrier molecule. Examples include:

mesalamine (5-aminosalicylic acid or 5-amino-2-hydroxybenzoic acid):

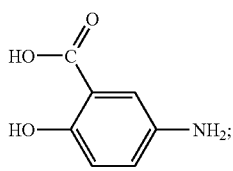

NO-mesalamine (5-amino-2-hydroxybenzoic acid 4-nitroxybutylester);

5-aminosalicylic acid derivatives, such as:

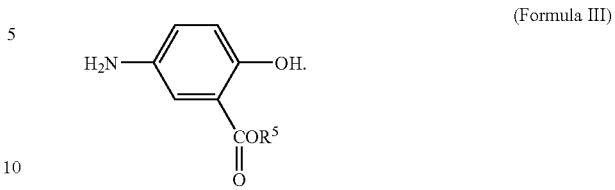

(Formula III)

Another class of 5-ASA compounds useful in the invention include 5-ASA compounds that are azo bonded to a carrier molecule. Examples include:

the 5-aminosalicylic acid dimer (olsalazine):

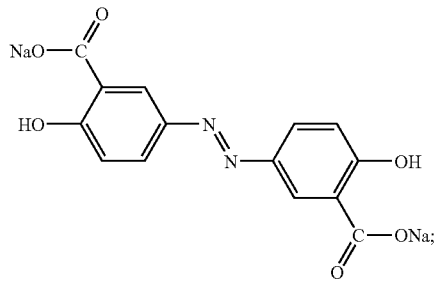

sulfasalazine (5-ASA chemically coupled via an azo group to sulfapyridine);

balsalazide ((E)-5-[[-4-[[(2-carboxyethyl)amino]carbonyl]phenyl]azo]-2-hydroxybenzoic acid disodium salt):

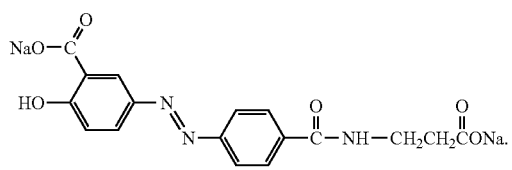

It will be appreciated that the APAZA™ compound described above, and the compounds of Formula II described above wherein $R^4$ is

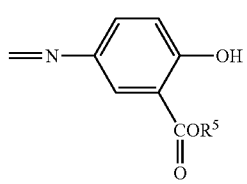

include 5-ASA components and 4-APAA components and are therefore considered 5-ASA compounds as well as 4-APAA compounds. Compounds that are both 5-ASA compounds and 4-APAA compounds can be specifically excluded from certain embodiments of the invention.

The carrier molecule can be active or inactive. Carrier molecules generally include a core phenylamine moiety:

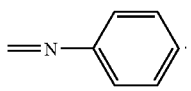

Preferred inactive carrier molecules are those exhibiting little or no toxicity; however, it will be appreciated that the degree of toxicity permitted must be balanced against the benefit of the drug. In one embodiment, the carrier molecules are chosen such that they are not readily absorbed into the bloodstream after cleavage of the azo bond in the intestine, so that a substantial amount of the carrier molecule leaves the body with the feces. It will be appreciated that a wide range of known structures can be employed as carrier molecules.

As discussed in more detail below, in some embodiments, the compositions and methods of the invention employ both a 5-ASA compound that is azo bonded to a carrier molecule and a 5-ASA compound that is not azo-bonded to a carrier molecule.

Other Therapeutic Agents

In addition to 4-APAA compounds and combinations of 4-APAA compounds with 5-ASA compounds described above, some aspects of the invention make use of other therapeutic agents in treatment methods and/or pharmaceutical compositions for the treatment of disorders involving inflammation of the digestive system or mucosal tissues. Examples include antibiotics, steroids, immune modulators, stool softeners, stool hardeners, nutraceuticals, probiotic agents and organisms, and nicotinic agents.

Antibiotics. The methods and compositions of the invention can include antibiotics. Examples include those antibiotics routinely used for treatment of inflammatory or ulcerative conditions of the bowel. Preferred examples include metronidazole (FLAGYL™), ciprofloxacin (CIPRO™), and rifaximin (made by Salix Pharmaceuticals, Inc., Raleigh, N.C.).

Steroids. The methods and compositions of the invention can include steroids, such as steroids routinely used for treatment of ulcerative conditions of the bowel. Examples of suitable steroids include prednisone, prednisolone, hydrocortisone, and budesonide.

Immune Modulators and/or Suppressants. The methods and compositions of the invention can include immune modulators. Examples include immune modulators routinely used for treatment of inflammatory or ulcerative conditions of the bowel. Preferred immune modulators include monoclonal antibody immune modulators, especially anti-TNF immune modulators, such as infliximab (REMICADE™), enteracept (ENBREL™), anakinra KINFRET™), adalimumab (HUMIRA™). Other suitable immune modulators include azathioprine, mercaptopurine (e.g., 6-mercaptopurine), 6-thioguanine, and methotrexate. Examples of suitable immunosuppressant compounds include cyclosporine and tacrolimus (PROGRAF™).

Probiotic Agents and Organisms and Nutraceuticals. The methods and compositions of the invention can include various probiotic agents and organisms and nutraceuticals for treating intestinal conditions. Examples include bacteria and/or nutrients used to treat intestinal conditions described herein, such as Crohn's disease, ulcerative colitis, radiation enteritis, pouchitis, diversion enteritis, acute diarrhea, traveler's diarrhea, antibiotic-associated diarrhea, *Helicobacter pylori* infection, and immunosuppression-associated diarrhea (e.g., AIDS-associated diarrhea). Examples of suitable probiotic agents include those used to promote enzymatic induction of disaccharidase activity, trophic effects on the intestinal mucosa, blocking of bacterial toxins, or induction of immunologic response. Examples of suitable probiotic organisms include *Lactobacillus, Bifidobacterium* and *Saccharomyces boulardii* (see, for example, Penna et al., "Up-to-date clinical and experimental basis for the use of probiotics," *J Pediatr* (Rio J). 76(Suppl. 1):S209-17 (2000), the entire disclosure of which is incorporated herein by reference).

Nicotinic agents. The methods and compositions of the invention can include various nicotinic agents and treatments, such as nicotine, in the treatment of inflammatory conditions of this invention (see, for example, Guslandi et al., "Distal ulcerative colitis refractory to rectal mesalamine: role of transdermal nicotine versus oral mesalamine," *Can J Gastroenterol.* 16(5):293-6 (2002), the entire disclosure of which is incorporated herein by reference).

Treatment Methods and Pharmaceutical Compositions

The invention provides treatment methods and pharmaceutical compositions for treating disorders involving inflammation of the digestive system or mucosal tissues. Examples of conditions suitably treated using the methods and compositions of the invention include inflammatory conditions of the mouth such as mucositis, infectious diseases (e.g., viral, bacterial, and fungal diseases), and Crohn's disease; inflammatory conditions of the esophagus such as esophagitis, conditions resulting from chemical injury (e.g., lye ingestion), gastroesophageal reflux disease, bile acid reflux, Barrett's esophagus, Crolm's disease, and esophageal stricture; inflammatory conditions of the stomach, such as gastritis (e.g., *Helicobacter pylori* infection, acid-peptic disease and atrophic gastritis), peptic ulcer disease, pre-cancerous lesions of the stomach, non-ulcer dyspepsia, and Crohn's disease; inflammatory conditions of the intestine, such as celiac disease, Crohn's disease, spastic colon, bacterial overgrowth, yeast imbalance, peptic ulcer disease, and fissures of the intestine, travellers' diarrhea, pouchitis, inflammatory bowel disease ("IBD," e.g., ulcerative colitis and Crohn's disease), and various forms of colitis, such as diversion colitis, non-specific colitis, ulcerative colitis, infectious colitis (e.g., pseudomembranous colitis such as *Clostridium difficile* colitis, salmonella enteritis, shigella infections, yersiniosis, cryptosporidiosis, microsporidial infections, and viral infections), radiation-induced colitis, colitis in the immunocompromised host (e.g., typhlitis), precancerous conditions of the colon (e.g., dysplasia, inflammatory conditions of the bowel, and colonic polyps), proctitis, inflammation associated with hemorrhoids, proctalgia fugax, and rectal fissures; liver, gallbladder and/or bilary tract conditions, such as hepatitis, cholangitis, sclerosing cholangitis, primary bilary cirrhosis, and cholecystitis; and intestinal abscess. The methods and compositions of the invention are also useful in the treatment of irritable bowel syndrome.

Treatment Methods

According to other embodiments of the present invention, methods of treating a subject in need of such treatment include administering an effective amount of a composition of this invention to the subject and/or delivering an effective amount of a composition of this invention to the digestive system and/or mucosal tissues of a subject. The effective amount will vary somewhat from composition to composition, and subject to subject, and will depend upon factors such as the age, species, gender and/or condition of the subject and the route and mode of delivery. Such dosages can be determined in accordance with routine pharmacological procedures known to those skilled in the art. In some embodiments, a dosage from about 100 µg to about 100 mg/kg will have efficacy, with all weights being calculated based upon the weight of the composition and/or active ingredient (e.g., 4-APAA compound). A dosage from about 10 mg/kg to about 50 mg/kg can be employed for oral administration. Typically, a dosage from about 0.5 mg/kg to 5 mg/kg can be employed for intramuscular injection. The frequency of administration can be one, two, or three times per day/week/month/year or as necessary to treat the condition. The duration of treatment depends on the type of condition being treated and can be for as long as the life of the patient.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention. Illustrative avians of the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes.

The method generally involves the administration of an effective amount of a 4-APAA compound, alone or in combination with other compounds as described herein, to a subject having a disorder involving inflammation of the digestive system and/or mucosal tissues. In certain embodiments, the disorder is a bowel condition, and the 4-APAA compound is administered as a component of a formulation that releases the 4-APAA compound in the lumen of the bowel in a manner which brings it into contact with a disease site, such as inflamed or ulcerated tissue (see, for example, Chourasia et al., "Pharmaceutical Approaches to Colon Targeted Drug Delivery Systems," *J Pharm Pharmaceut Sci* 6(1):33-66 (2003), the entire disclosure of which is incorporated herein by reference).

The 4-APAA compound can be administered as a monotherapy. Alternatively, the 4-APAA compound can be administered as a component of a combination therapy regimen employing at least one 4-APAA compound and one or more other compounds. Where a combination therapy is used, the various therapeutic compounds can be administered separately or together as components of a single formulation. The following table provides illustrative examples:

| No | Compound 1 | Compound 2 | Other Compounds |
|---|---|---|---|
| 1 | Azo bonded 4-APAA compound | Non-azo bonded 5-ASA compound | Optional |
| 2 | Non-azo bonded 4-APAA compound | Azo bonded 5-ASA compound | Optional |
| 3 | Azo bonded 4-APAA compound | Non-azo bonded 4-APAA compound | Optional |
| 4 | Azo bonded 5-ASA compound | Non-azo bonded 5-ASA compound | Optional |
| 5 | APAZA ™ compound | Non-azo bonded 5-ASA compound | Optional |
| 6 | APAZA ™ compound | Non-azo bonded 4-APAA compound | Optional |
| 7 | APAZA ™ compound | Non-azo bonded 5-ASA compound | Non-azo bonded 4-APAA compound |
| 8 | Non-azo bonded 4-APAA compound | Azo bonded 5-ASA compound | Local steroid (e.g., budesonide) |
| 9 | Non-azo bonded 4-APAA compound | Azo bonded 5-ASA compound | Antibiotic |

Depending on the specific condition or disease state to be treated, subjects are administered compounds of the present invention at any suitable therapeutically effective and safe dosage, as can readily be determined within the skill of the art and without undue experimentation in light of the present disclosure. For example, the 4-APAA compound is suitably administered in an amount ranging from about 0.001 mg/kg·day to about 500 mg/kg·day, from about 0.01 mg/kg·day to about 100 mg/kg·day, from about 0.1 mg/kg·day to about 10 mg/kg·day, or about 1 mg/kg·day.

The 4-APAA compounds, 5-ASA compounds, and other compounds used in the compositions and methods of the invention can be administered or delivered per se as well as in the form of pharmaceutically acceptable esters, salts, and other physiologically functional derivatives thereof and/or in a pharmaceutically acceptable carrier.

Formulations

The invention provides pharmaceutical formulation compositions for use in the methods of the invention. The pharmaceutical formulations are selected to facilitate delivery of a 4-APAA compound to a subject. The 4-APAA compound can be administered alone or with one or more additional therapeutic compounds, such as a second 4-APAA compound, a 5-ASA compound and/or any compound as described herein.

In the manufacture of a pharmaceutical composition according to embodiments of the present invention, the therapeutic agent(s) is typically admixed with, inter alia, a pharmaceutically acceptable carrier. The carrier must, of course, be acceptable in the sense of being compatible with any other ingredients in the pharmaceutical composition and should not be deleterious to the subject. The carrier may be a solid or a liquid, or both, and is preferably formulated with the therapeutic agent(s) as a unit-dose formulation, for example, a tablet, which may contain from about 0.01 or 0.5% to about 95% or 99% by weight of the therapeutic agent(s). The pharmaceutical compositions may be prepared by any of the well-known techniques of pharmacy including, but not limited to, admixing the components, optionally including one or more accessory ingredients. The therapeutic agent(s) are provided in an amount effective to achieve the desired pharmacological effect, as described above, and in a quantity appropriate to achieve the desired daily dose.

In certain embodiments, the compositions of the invention are designed to deliver the therapeutic agent(s) to the site of disease. For example, where the condition is Crohn's disease, an oral composition can be formulated to deliver the therapeutic agent(s) to ulcerated or inflamed tissue in the large intestine and/or the colon, releasing the therapeutic agent(s) along the length of the small intestine and the colon, and/or along the distal portion of the small intestine and in the colon. Similarly, where the disease condition is ulcerative colitis, an oral composition can be formulated to release the therapeutic agent(s) along the length of the distal portion of the small intestine and in the colon, or along the length of the colon. Moreover, where the disease site is in the colon (e.g., ulcerative colitis), the therapeutic agent(s) can be formulated as a suppository or an enema.

Other suitable formulations include, for example, oral compositions such as mouth washes for treatment of inflammatory conditions of the oral cavity or throat; vaginal compositions for treatment of inflammatory conditions of the vaginal cavity or opening; intra-uterine formulations for inflammatory conditions of the uterus; eye formulations, such as eye-drops or salves for treatment of inflammatory conditions of the eye or conjunctiva; as well as topical formulations for dermal application to treat inflammatory conditions of the skin.

Formulations of the present invention suitable for oral administration can be presented as discrete dosage units such as capsules, cachets, tablets, or lozenges, each containing a predetermined amount of a 4-APAA compound, optionally with a 5-ASA compound, a second 4-APAA compound, and/or other therapeutic compound. The therapeutic agent component of the formulation can, for example, take the form of a powder or granules. Granules can themselves be coated, e.g., enterically coated. The formulations can also suitably be provided as suspensions, e.g., in an aqueous liquor or a non-aqueous liquid, such as a syrup, an elixir, an emulsion, or a draught.

Oral formulations for treatment of intestinal conditions are preferably solid dosage forms and can include any of a wide variety of components known to assist therapeutic agents to pass through the stomach and be released in the intestine, such as in the proximal small intestine, distal small intestine, and/or in the colon. Moreover, the compositions can be prepared to release a first agent in the stomach and one or more additional agents in the small intestine or colon. Examples of such strategies are described in the following table:

| No. | Stomach | Small Intestine | Distal Small Intestine | Colon |
|---|---|---|---|---|
| 1 | 5-ASA compound | None | 5-ASA compound and 4-APAA compound | 5-ASA compound and 4-APAA compound |
| 2 | 5-ASA compound | 5-ASA compound | 5-ASA compound and 4-APAA compound | 5-ASA compound and 4-APAA compound |
| 3 | 5-ASA compound | None | None | 5-ASA compound and 4-APAA compound |
| 4 | 5-ASA compound | 5-ASA compound | None | 5-ASA compound and 4-APAA compound |
| 5 | 4-APAA compound | None | 5-ASA compound and 4-APAA compound | 5-ASA compound and 4-APAA compound |
| 6 | 4-APAA compound | 4-APAA compound | 5-ASA compound and 4-APAA compound | 5-ASA compound and 4-APAA compound |
| 7 | 4-APAA compound | None | None | 5-ASA compound and 4-APAA compound |
| 8 | 4-APAA compound | 4-APAA compound | None | 5-ASA compound and 4-APAA compound |
| 9 | None | None | 5-ASA compound and 4-APAA compound | 5-ASA compound and 4-APAA compound |
| 10 | None | 5-ASA compound | 5-ASA compound and 4-APAA compound | 5-ASA compound and 4-APAA compound |
| 11 | None | None | None | 5-ASA compound and 4-APAA compound |
| 12 | None | 5-ASA compound | None | 5-ASA compound and 4-APAA compound |
| 13 | None | None | 5-ASA compound and 4-APAA compound | 5-ASA compound and 4-APAA compound |
| 14 | None | 4-APAA compound | 5-ASA compound and 4-APAA compound | 5-ASA compound and 4-APAA compound |
| 15 | None | None | None | 5-ASA compound and 4-APAA compound |

| No. | Stomach | Small Intestine | Distal Small Intestine | Colon |
|---|---|---|---|---|
| 15 | None | 4-APAA compound | None | 5-ASA compound and 4-APAA compound |

Preferred components for compositions for oral administration for delivery of the therapeutic agent to a disease site in the small intestine or colon include the following: one or a combination of components selected from the group consisting of: AZO-bonded coatings, enteric coatings, pH sensitive coatings, coatings that dissolve in a pH range of about 5.5 to about 7, methacryllic polymers, time release coatings, microcapsules, biodegradable coatings, and redux sensitive coatings.

Synthetic Methods

Figure 1:
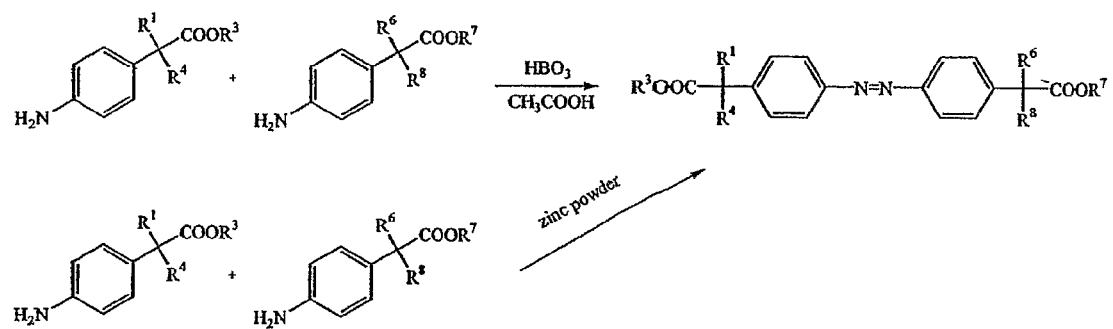
FIGS. 1 and 2 illustrate embodiments of synthesis routes for APAZA™ compounds used in the present invention.
Figure 2:
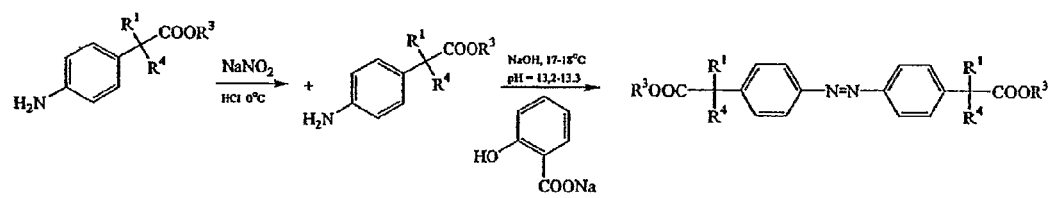

The therapeutic agents of the present invention are either available commercially or can be made according to methods of the invention using known starting materials and reagents. For example, the synthetic paths illustrated in FIGS. 1 and 2 are useful for making the APAZA™ therapeutic agent and related compounds. Variations on the disclosed general synthetic methods will be readily apparent to those of ordinary skill in the art and are deemed to be within the scope of the present invention.

Particular aspects of the present invention will now be described with reference to the following examples. It should be appreciated that these examples are for the purposes of illustrating aspects of the present invention, and do not limit the scope of the invention.

EXAMPLES

Synthesis of Compounds of the Present Invention

Melting points were taken on a Laboratory Devices Mel-Temp II capillary melting point apparatus and are uncorrected. $^1$HNMR spectra were obtained on a Varian Unity 600 MHz spectrometer. Chemical shifts (d) are reported as parts per million (ppm) relative to the internal standard tetramethylsilane. Ultraviolet and visible spectra were obtained with a Beckman DU 640i spectrophotometer. Infrared spectroscopy was obtained on a Nicolet Impact 410 and fast atom bombardment (FAB) mass spectroscopy data was obtained by M-Scan Inc. All reagents were used as received from Aldrich Chemical Co.

Synthesis of 5-[4-(1-carboxy-ethyl)-phenylazo]-2-hydroxy-benzoic acid 2-(4-Amino-phenyl)-propionic acid. A 500-mL, oven dried, three-neck flask equipped with a stir bar, was charged with (R,S) 2-(4-nitrophenyl)propionic acid (5.00 g, 25.6 mmol), absolute ethyl alcohol (200 mL), and palladium (10 wt. % on activated carbon, 0.27 g, 2.56 mmol). A hydrogen environment was introduced into the flask and the mixture was then stirred at ambient temperature for 6 hours. The crude reaction mixture was filtered through Celite and the ethyl alcohol was removed under reduced pressure. The crude product was dried under vacuum overnight resulting in a light yellow solid (70% yield, 2.98 g): mp 125-129° C., $^1$H NMR (DMSO-d$_6$): d 1.24 (3H, s), 1.26 (3H, s), 3.41 (1H, s), 3.43 (2H, s), 6.46 (2H, d, J=7.6 Hz), 6.91 (2H, d, J=7.6 Hz); IR (KBr) 2596, 2189, 1630, 1581, 1441, 1375, 1277, 1192, 1052, 876 cm$^{-1}$; FAB-MS (NBA) m/z 165 (M+H)$^+$.

5-[4-(1-carboxy-ethyl)-phenylazo]-2-hydroxy-benzoic acid. As prepared in the above procedure, 2-(4-amino-phenyl)-propionic acid (3.90 g. 23.6 mmol) dissolved in an aqueous HCl solution (75 mL, 36.5-38.0% HCl in 8 mL H$_2$O) was placed in a 200-mL beaker and cooled to 0° C. in an ice bath. When the solution was stabilized at 0° C., sodium nitrite (1.79 g, 26.0 mmol) in water (2 mL) was added dropwise. The temperature was maintained at 0-5° C. and the resulting diazonium salt solution stirred for 15 min.

While the diazonium salt solution stirred, an 800-mL beaker fitted with a stir bar, thermometer, and pH probe (Orion model 420A with Orion semimicro pH probe) was charged with salicylic acid, sodium salt (11.3 g, 20.8 mmol) dissolved in sodium hydroxide (4.25 g, 106 mmol) and H$_2$O (100 mL). Using an ice bath, the salicylic acid solution was cooled to 17° C. and the diazonium salt solution was slowly added in 10 mL portions. Throughout the addition, the pH was maintained at 13.2-13.3 with the addition of aqueous sodium hydroxide, and the temperature was kept between 17-18° C. with the addition of ice. After the addition was complete, the resulting dark red solution was allowed to warm to ambient temperature and stirring was continued for 90 min. Upon acidification to pH 3.5 with concentrated HCl (~20 mL, 36.5-38%), a dark red solid precipitated and was collected by vacuum filtration.

The crude product (8.49 g, 27.0 mmol) was suspended in H$_2$O (300 mL) and heated at 70° C. for 30 min. to remove excess salicylic acid. The suspension was cooled to 50° C. and a solid was collected by suction filtration. The collected solid was then purified by flash chromatography (SiO$_2$: ethyl acetate/hexanes, 1:1). The crude product (2.50 g. 7.95 mmol) in DMF (~4.5 mL) was loaded and yellow colored fractions were collected, combined, and concentrated under reduced pressure. After drying under vacuum, the purified product was obtained as an orange solid in 55% yield (1.38 g): mp 147° C., $^1$H NMR (DMSO-d$_6$): d 1.38 (3H, s), 1.39 (3H, s), 3.76 (1H, s), 3.78 (1H, s), 7.11 (1H, d, J=8.4 Hz), 7.46 (2H, d, J=7.8 Hz), 7.80 (2H, d, J=8.4 Hz), 8.03 (1H, d, J=9.0 Hz), 8.30 (1H, s); IR (KBr) 2973, 1921, 1708, 1652, 1577, 1477, 1339, 1289, 1226, 1164, 1101, 1013, 857, 663 cm$^{-1}$; UV-Vis (MeOH) ?$_{max}$=355 nm, e=23,700 mol$^{-1}$ cm$^{-1}$L; FAB-MS (NBA) m/z 313 (M)$^-$.

Synthesis of 5-(4-carboxymethyl-phenylazo)-2-hydroxy-benzoic acid [APAZA™ therapeutic agent]

4-Aminophenylacetic acid (10.0 g, 66.2 mmol) dissolved in an aqueous HCl solution (20 mL, 36.5-38.0% HCl in 200 mL H$_2$O) was placed in a 500-mL beaker and cooled to 0° C. in an ice bath. When the solution was stabilized at 0° C., sodium nitrite (5.02 g, 72.8 mmol) in water (50 mL) was added slowly in 5 mL portions. The temperature was maintained at 0-5° C. and the resulting diazonium salt solution stirred for 15 min.

While the diazonium salt solution stirred, a 2 L beaker fitted with a stir bar, thermometer, and pH probe (Orion model 420A with Orion semimicro pH probe) was charged with salicylic acid, sodium salt (31.8 g, 198 mmol) dissolved in sodium hydroxide (11.9 g, 230 mmol) and water (200 mL). Using an ice bath, the salicylic acid solution was cooled to 17° C. and the diazonium salt solution was slowly added in 25 mL portions. Throughout the addition, the pH was maintained at 13.2-13.3 with the addition of aqueous sodium hydroxide, and the temperature kept between 17-18° C. with the addition of ice. After the addition was complete, the resulting dark red solution was allowed to warm to ambient temperature and stirring was continued for an additional 30 min. Upon acidification to pH 3 with concentrated HCl (~50 mL, 36.5-38%), a brown solid precipitated and was collected by suction filtration.

The crude product was purified by flash chromatography ($SiO_2$: ethyl acetate/hexanes, 1:1). On a column packed with 70-230 mesh, 60 Å silica gel with BET surface area of ~500 $m^2/g$ and pore volume of 0.75 $cm^3/g$, the crude product (11.5 g, 38.2 mmol) in DMF (~12 mL) was loaded. Fractions were collected and combined based on color. The first band was yellow in color and contained excess salicylic acid as well as traces of the desired product. The second band was orange and contained the desired product, and the third band was red and contained unknown impurities. All fractions were combined and concentrated under reduced pressure and dried under vacuum.

The purified product was obtained as an orange solid in 28% yield (2.75 g): mp 204° C.; $^1$H NMR (DMSO-$d_6$), d 3.67 (2H, s), 7.11 (1H, d, J=9.0 Hz), 7.44 (2H, d, J=8.4 Hz), 7.79 (2H, d, J=8.4 Hz), 8.02 (1H, d of d, J=2.4 Hz, 9.0 Hz), 8.29 (1H, s); IR (KBr) 3098, 1696, 1614, 1458, 1345, 1195, 838 $cm^-$; UV-Vis (MeOH) $?_{max}$=350 nm, e=25,700 $mol^{-1}$ $cm^{-1}$ L; positive FAB-MS (NBA) m/z 301 (M+H)$^+$, negative FAB-MS(NBA) m/z 299 (M)$^-$.

Synthesis of
4-(4-Carboxymethyl-Phenylazo)-Phenylacetic Acid

4-Aminophenylacetic acid (3.75 g, 24.8 mmol) was suspended in water (75 mL) and concentrated hydrochloric acid (8 mL) was added. The solution was cooled to 0° C. in an ice bath with rapid stirring. Sodium nitrite (1.80 g, 26.1 mmol) in water (20 mL) was added dropwise to the 4-aminophenylacetic acid solution with rapid stirring. Care was taken to keep the temperature between 0-5° C. at all times, especially during the $NaNO_2$ addition. The reaction was stirred for an additional 20 min. In the meantime, phenylacetic acid (10.1 g, 74.4 mmol) was dissolved in an aqueous NaOH solution (4.50 g, 113 mmol NaOH in 100 mL $H_2O$). The solution was vigorously stirred at 17° C. and at pH 13.3. The diazonium salt solution was added dropwise to the phenylacetic acid solution. It is of utmost importance to keep the temperature of the phenylacetic acid solution between 17-18° C. and the pH between 13.2-13.3 at all times, especially during the diazonium salt addition. The temperature was regulated by the addition of ice and the pH regulated by the addition of 8 M NaOH. After addition was complete, the solution was allowed to warm to room temperature and stirred for an additional 30 min. The reaction mixture was suction filtered to remove any undissolved particulates or unwanted side products. The filtrate was acidified with aqueous HCl (10 mL conc. HCl in 20 mL $H_2O$), which produced a dark red precipitate. The precipitate was collected by suction filtration and washed several times with cold $H_2O$, until the filtrate was clear. The collected solid was air dried overnight to give the desired compound as a red solid in 37% yield: IR (KBr) 3030 (br), 1696, 1658, 1452, 1414, 1201, 850, 675 $cm^{-1}$ FABMS m/z 299 (M+H)$^+$, 320 (M+Na); $^1$H NMR (DMSO-$d_6$), d 3.47 (s, 4H), 7.33 (4H, d, J=8.1 Hz), 7.84 (4H, d, J=8.4 Hz).

Metabolism of APAZA™ Following Oral Delivery

The degradation of the APAZA™ therapeutic agent (5-(4-carboxymethyl-phenylazo)-2-hydroxy-benzoic acid), and sulfasalazine (used as a control) and the generation of their metabolites when these compounds were orally dosed to rats were measured to be able to confirm that both the APAZA™ therapeutic agent and sulfasalazine undergo bacterial azo reduction and yield their metabolites, 5-aniinosalicylic acid (5-ASA) and sulfapyridine for sulfasalazine, 5-aminosalicylic acid (5-ASA) and 4-aminophenyl acetic acid (4-APAA) for the APAZA™ therapeutic agent.

This experiment was performed to confirm that an azo compound, the APAZA™ therapeutic agent, undergoes a bacterial reduction process and yields its metabolites in in-vivo metabolism. The quantification of its metabolites was also carried out. Sulfasalazine, not part of the present invention, was used as a control since similar azo bond cleavage by bacteria occurs with it, which results in 5-aminosalicylic acid and sulfapyridine as its metabolites. Both the APAZA™ therapeutic agent and sulfasalzine were degraded and their metabolites were produced as expected.

For urine, the parent compounds and their metabolites were detected with day 1 collection only. The rest of the collections did not show any compounds. For feces, compounds were detectable up to day 2 collection.

Rats that were dosed with the APAZA™ therapeutic agent (rat 1, 2, and 3) showed the APAZA™ therapeutic agent, 4-APAA, actarit, and acetylated 5-ASA in urine. Rats with sulfasalazine dosage (rat 4, 5, and 6) showed sulfasalazine, sulfapyridine, and acetylated 5-ASA in urine. Only acetylated 5-ASA was detected in feces regardless of what compounds were given. 5-ASA was quickly converted to acetylated 5-ASA.

It is interesting to note that while sulfasalazine dosed rats produced their metabolites, 5-ASA (acetylated 5-ASA in this case) and sulfapyridine, in 1:1 ratio, rats with the APAZA™ therapeutic agent dosage produced 7 to 10 times more of 4-APAA than acetylated 5-ASA.

It is believed that the majority of the ingested sulfasalazine travels down the small intestine to the colon and undergoes bacterial azo reduction to liberate sulfapyridine and 5-ASA compounds. The results from this study confirm this belief and show that the APAZA™ therapeutic agent undergoes a similar bacterial azo reduction.

A total of 8 rats were used for the experiment and methylcellulose was used as a vehicle. The dosage amount was 100 mg/kg per rat. Three rats were dosed with the APAZA™ therapeutic agent and the other three rats were dosed with sulfasalazine. Two rats were used as a control and dosed with methylcellulose. Both urine and feces were collected over 4 days and analyzed by HPLC.

Urine was collected each day and 300 µL of aliquot from each sample was centrifuged for 10 minutes at 5000 g. 80 µL of supernatant was injected for analysis. Feces was also collected each day and homogenized with 1:1 mixture of water and acetonitrile. This mixture was then centrifuged for 20 minutes at 5000 g. 80 µL of supernatant was injected for analysis.

A water 2690 HPLC was used for sample analysis as follows:
Mobile phase programming: Gradient
Mobile phase: A=Water+0.1% TFA; B=Acetonitrile+0.1% TFA
Flow rate: 1 mL/min.
Column: Phenomenex Max RP, 80 Å, 4.6 mm×250 mm
PDA settings: Collected spectrum: 210-400 nm; extracted chromatogram: 280 and/or other
Run time/sample: Approximately 50 min.

| Time | Flow (mL/minute) | % Mobile Phase A | % Mobile Phase B |
|---|---|---|---|
| — | 1 | 100 | 0 |
| 40 | 1 | 50 | 50 |
| 43 | 1 | 5 | 95 |
| 44 | 1 | 95 | 5 |
| 50 | 1 | 95 | 5 |

5-ASA was quickly converted to acetylated 5-ASA (5-aceASA). The same amount of acetylated 5-ASA was generated from both the APAZA™ therapeutic agent and sulfasalazine in urine. Acetylated 5-ASA and sulfapyridine were produced in 1:1 ratio from sulfasalazine dosed rat urine. Approximately 7 to 10 times more of 4-APAA was produced than acetylated 5-ASA from the APAZA™ therapeutic agent dosed rat urine. Only acetylated 5-ASA was detected from feces regardless of dosed compound. More acetylated 5-ASA was detected in feces than urine.

Day 1 the APAZA™ therapeutic agent Dosed

| | Total Dosage (mg) | the APAZA™ therapeutic agent (mg) | 4APAA (mg) | Actarit (mg) | Acetylated 5ASA (mg) |
|---|---|---|---|---|---|
| Urine | | | | | |
| Rat 1 | 22.0 | 0.48 | 3.456 | 0.0717 | 0.299 |
| Rat 2 | 23.5 | 0.3546 | 3.177 | | 0.422 |
| Rat 3 | 22.5 | 0.4707 | 4.674 | | 0.298 |

Sulfasalazine Dosed

| | Total Dosage (mg) | Sulfasalazine (mg) | Sulfapyridine (mg) | Acetylated 5ASA (mg) |
|---|---|---|---|---|
| Rat 4 | 21 | 0.00882 | 0.337 | 0.288 |
| Rat 5 | 22.5 | 0.01279 | 0.305 | 0.328 |
| Rat 6 | 21 | 0.01092 | 0.41 | 0.39 | the APAZA™ therapeutic agent Dosed

| | Total Dosage (mg) | Acetylated 5ASA (mg) |
|---|---|---|
| Stool | | |
| Rat 1 | 22 | 1.9254 |
| Rat 2 | 23.5 | 1.9519 |
| Rat 3 | 22.5 | 1.2437 |

| | Total Dosage (mg) | Acetylated 5ASA (mg) |
|---|---|---|

Sulfasalazine Dosed

| | Total Dosage (mg) | Acetylated 5ASA (mg) |
|---|---|---|
| Rat4 | 21 | 1.2158 |
| Rat5 | 22.5 | 1.3708 |
| Rat6 | 21 | 0.9033 |

Day 2 the APAZA™ therapeutic agent Dosed

| | Total Dosage (mg) | Acetylated 5ASA (mg) |
|---|---|---|
| Stool | | |
| Rat 1 | 22 | 0.2562 |
| Rat 2 | 23.5 | 0.7755 |
| Rat 3 | 22.5 | 0.1827 |

Sulfasalazine Dosed

| | Total Dosage (mg) | Acetylated 5ASA (mg) |
|---|---|---|
| Rat 4 | 21 | 0.2 |
| Rat 5 | 22.5 | 0.2584 |
| Rat 6 | 21 | 0.1458 |

Biological Effects of Compounds of the Present Invention

The purpose of this study was to histologically evaluate and compare the effects of three different therapeutic agents administered intrarectally (twice daily for four days) to male Lewis rats following intrarectal administration of dinitrobenzene sulfonic acid (DNBS). DNBS induced colitis in rats according to an established experimental model (see, for example, Bertran et al., "Intracolonic administration of zileuton, a selective 5-lipoxygenase inhibitor, accelerates healing in a rat model of chronic colitis," *Gut.* 38(6):899-904 (1996), and Blau et al., "Relation between colonic inflammation severity and total low-molecular-weight antioxidant profiles in experimental colitis," *Dig Dis Sci.* 45(6):1180-1187 (2000), the entire disclosures of which are incorporated herein by reference). SHAM and DNBS groups served as negative and positive controls, respectively. The distribution of animals to each group is presented in Table 1:

| GROUP | NUMBER OF ANIMALS |
|---|---|
| SHAM | 6 |
| DNBS | 5 |
| 5-ASA | 6 |
| 4-APAA | 6 |
| Mixture of 5-ASA and 4-APAA | 4 |

Trimmed specimens of colon from 27 male rats were tested, including microtoming, and hematoxylin and eosin staining. The resulting 27 slides (1 transverse section per slide) were examined microscopically. Except for one rat from the SHAM group and one rat from the DNBS group, all slides had their labels taped over to facilitate blind reading. Lesions were graded on a scale of 1-5 (1=minimal; 2=mild; 3=moderate; 4=moderately-severe; 5=severe).

The principal histomorphologic change observed in the colon sections of all rats treated with DNBS (regardless of any additional treatment) was partial to full-thickness, full-length, coagulative-type necrosis. Necrosis was not observed in the saline/methylcellulose treated rats (SHAM group). In all cases, necrotic areas were characterized by a dramatic loss of cellular detail and staining affinity; in such areas only "ghost" outlines of the colonic architecture remained. Occasionally, segmental collapse or "dropout" of an intestinal tissue layer was evident. Necrotic tissues were heavily invaded by mixed types of bacteria. In sections that were not completely necrotic, the pattern of necrosis tended to be laminar, typically affecting the mucosa and submucosa while sparing portions of the muscularis externa and/or aciventitia (serosa and adjacent mesentery). In these sections, a dense zone of karyorrhectic neutrophils divided the necrotic inner layers from the less affected outer layers. Fibrinoid necrotizing vasculitis of submucosal blood vessels was observed in all DNBS-treated rats. Vasculitis was observed in both necrotic and non-necrotic regions, often accompanied by thrombosis (fibrinous, fibrinocellular, and/or bacterial thrombi), and minimal to moderate submucosal hemorrhage (with or without fibrin accumulation). Some hemorrhagic sites contained pigment-laden macrophages (siderophages—not separately diagnosed). In all sections from DNB S-treated rats, the serosa and adjoining mesentery were expanded by mild to moderately severe fibrovascular proliferation (early granulation tissue).

Sections from two rats (#4 and #11, Mixture of 5-ASA and 4-APAA group), each contained a single, short, sharply demarcated segment of non-necrotic, non-ulcerated mucosa. Changes within these comparatively unaffected mucosal segments were limited to minimal to mild crypt epithelial hyperplasia, minimal crypt dilation, and minimal neutrophilic infiltration.

Severity scoring of colonic necrosis was based upon the degree of tissue involvement; however, grade 5 (severe) was reserved for lesions in which necrosis resulted in extensive tissue loss. Because the pattern of necrosis often varied from section to section, the individual intestinal layers were scored separately. Generally, the average severity scores for necrosis were comparable among the four groups of DNBS-treated rats, shown in the following table:

| Group | SHAM | DNBS | 5-ASA | 4-APAA | Mixture 5-ASA & 4-APAA |
|---|---|---|---|---|---|
| No. Animals | (6) | (5) | (6) | (6) | (4) |
| Mucosa | 0.00 | 4.20 | 4.50 | 4.33 | 3.50 |
| Submucosa | 0.00 | 4.20 | 4.17 | 4.00 | 4.25 |
| Muscularis | 0.00 | 3.60 | 3.5 | 3.17 | 3.00 |
| Adventitia | 0.00 | 1.40 | 1.67 | 1.67 | 1.50 |

The average score for mucosal necrosis in the Mixture of 5-ASA and 4-APAA group was lower than scores in the other groups of DNBS-treated rats due to the spared areas of mucosa in two animals from the Mixture of 5-ASA and 4-APAA group.

The principal histomorphologic change observed in the colon sections of all rats treated with DNBS (regardless of any additional treatment) was partial to full-thickness, full-length, coagulative-type necrosis. Associated changes included massive bacterial invasion of the necrotic tissue, fibrinoid necrotizing vasculitis with thrombosis and hemorrhage, and heavy neutrophilic infiltration. Necrosis was not observed in the saline/methylcellulose-treated rats (SHAM group). The severity (extent) of necrosis was comparable among the four groups of DNBS-treated rats (DNBS, 5-ASA, 4-APAA, and Mixture of 5-ASA and 4-APAA), except that single segments of mucosa were comparatively spared in 2/4 rats from the Mixture of 5-ASA and 4-APAA group.

Anti-Inflammatory Activity of Drug Mixture

Dinitrobenzene sulfonic acid (DNBS) colitis was induced (no ether anesthesia) in 4 groups 4 of 6 Lewis rats each. One DNBS group was dosed with vehicle (0.7% methyl cellulose) as well as an additional sham group of 6 animals that received a saline enema instead of DNBS. Intrarectal (ir) dosing was performed in conscious animals b.i.d. for 4 days. Drug treatments were as follows:

5-aminosalicylic acid (5-ASA): 50 mg/kg
4-aminophenylacetic acid (4-APAA): 49.5 mg/kg (equimolar to 5-ASA)
Mixture: 5-ASA+4-APAA: 50 mg/kg+49.5 mg/kg Drugs were suspended in the above mentioned vehicle and staff blinded to drug groups. Daily weights and diarrhea scores were recorded. On the 5th day post-irritant rats were sacrificed, laparotomies performed and scored for intestinal adhesions and strictures; colectomized and colon weights recorded, colons opened longitudinally and inflammation/ulcerations scored.

Figure 3:
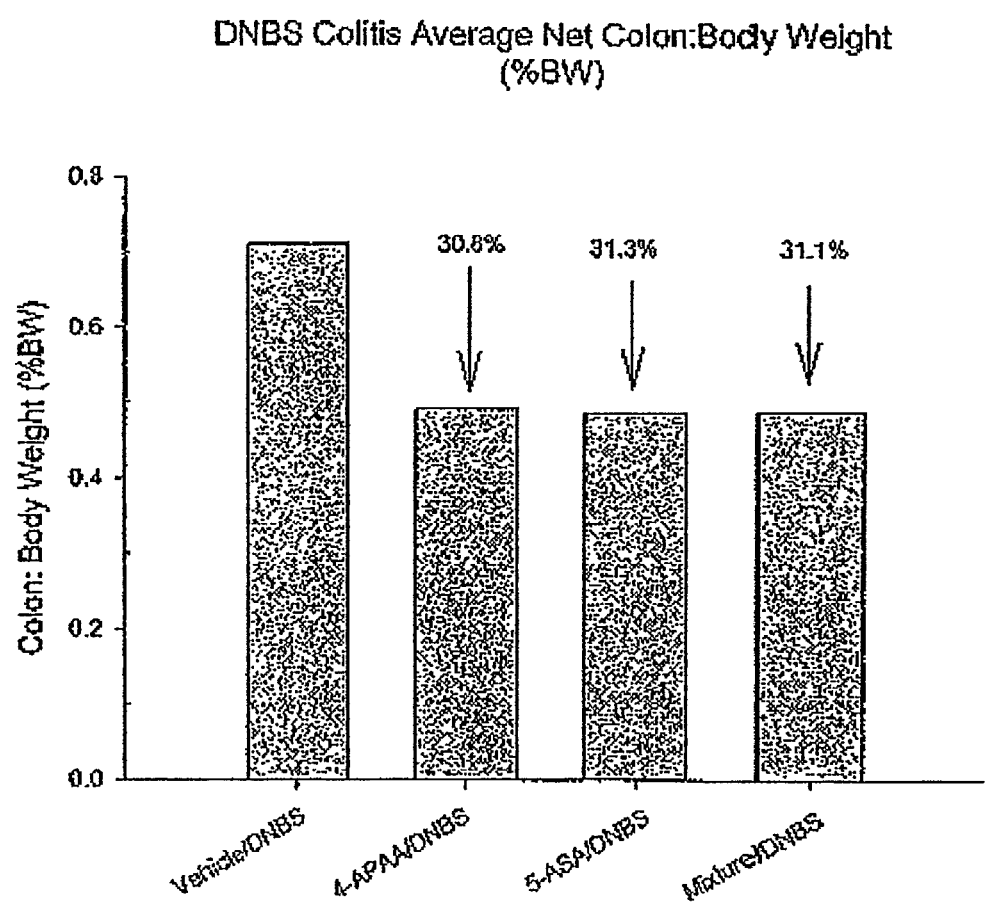
FIG. 3 illustrates the average reduction in colon:body weight [% BW] utilizing embodiments of the present invention (4-APAA/DNBS and Mixture/DNBS) in comparison with results achieved by 5-ASA/DNBS and control (Vehicle/DNBS).
Figure 4:
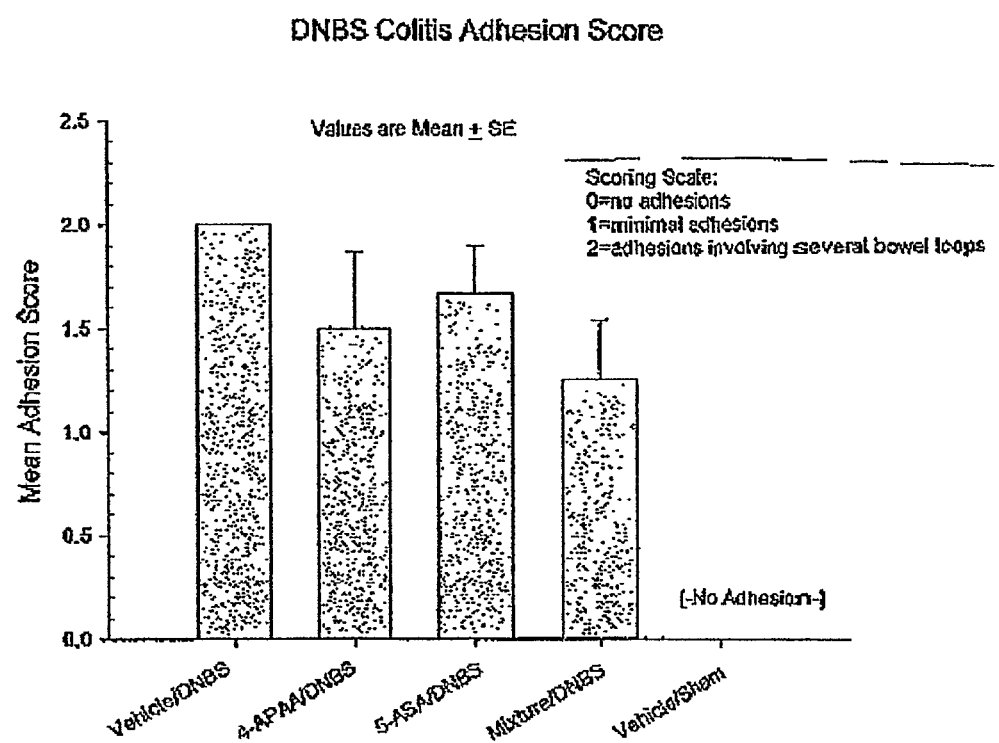
FIG. 4 illustrates DNBS colitis adhesion scores achieved utilizing embodiments of the present invention (4-APAA/DNBS and Mixture/DNBS) in comparison with results achieved by 5-ASA/DNBS and control (Vehicle/DNBS and Vehicle/Sham).

Results illustrated in FIGS. 3 and 4 indicated that 5-ASA, 4-APAA, and the mixture produce similar anti-inflammatory activity (~31% reduction in colon:body weight [% BW]). The severity of inflammation approached maximum. It is possible that the severity could be titrated by reduction of the DNBS dose and a small study was performed to test this hypothesis. It is possible that with a milder insult there can be evidence of greater separation of treatment effects.

DNBS colitis was induced in 6 Lewis rats (3 at 30 mg per rat and 3 at 15 mg per rat DNBS) and allowed to develop for 5 days with no treatment in order to determine the severity of inflammation. Diarrhea was noted on days 1-4 and the rats were sacrificed on day 5, scored, and colon:body weight determined. Results indicate that 15 mg per rat DNBS produces milder but inconsistent inflammation compared to 30 mg per rat. The 30 mg DNBS result was consistent with that seen previously.

Pharmacokinetic Studies

Initial single dose pharmacokinetic studies with the APAZA™ compound have been conducted in dogs and mice. A study was completed in order to determine the plasma pharmacokinetics and elimination of the APAZA™ compound and its metabolites (5-ASA, 4-APAA, 5-aceASA and 4-aceAPAA) following single oral dose administration to male CD-1 mice. For APAZA™ the $C_{max}$, $AUC_\infty$, and $t_{1/2}$ values were 5.93 µg/mL, 7.43 µg/mL h and 3.34 h. When normalized to molar values, the $C_{max}$ values for all the APAZA™ metabolites were less than APAZA™; the values ranged from 2.68 to 13.8 µM. However, the normalized APAZA™ $AUC_\infty$ value was not greater than all the other metabolites; these values ranged from 11.2 to 111 µg/M·h. With the exception of acetylated 5-ASA, the $t_{1/2}$ values for the metabolites ranged from 1.06-3.34 hours. The $t_{1/2}$ value for acetylated 5-ASA was 11.27 hours. The plasma concentrations for APAZA™, 4-APAA, 5-aceASA, and 4-aceAPAA were below the limit of detection at 24 hours. The $T_{max}$ values for APAZA™ and its metabolites were 1 hour and 4 hours, respectively. APAZA™ and its metabolites were eliminated through both fecal and urinary pathways with 44.5% of the dose recovered as APAZA™, 5-ASA, 4-APAA, 5-aceASA or 4-aceAPAA by 24 hours.

APAZA™ plasma levels increased in a dose-related manner over the dose range of 100 to 1000 mg/kg when administered as a single oral dose to Beagle dogs. Oral administration of a single dose of 1000 mg/kg to dogs resulted in an APAZA™ mean maximum plasma concentration ($C_{max}$) of 9.78 µg/mL in males and 2.64 µg/mL in females, time to maximum plasma concentration ($t_{max}$) of 15.0 and 24.0 hours in males and females, respectively, area under the plasma concentration-time curve ($AUC_{0-t}$) of 95.4 µg·h/mL and 40.8 µg·h/mL for male and female dogs, respectively.

The effects of 5-ASA, 4-APAA and APAZA™ therapeutic agent were compared in studies using 2,4-dinitrobenzenesulfonic acid (DNBS), dextran sulfate sodium (DSS) and Toxin A models of colitis in rats. In a DSS model of chronic colitis APAZA™ compound preserved normal colon histologic structure and prevented an increase in colon wet weight: body weight ratio; both, if abnormal, are indicators of colitis. Effects following administration of equimolar doses of both oral and rectal APAZA™ compound and sulfasalazine in a DNBS model of colitis indicate that both compounds have soirne activity. Results from studies completed in the toxin A model of acute colitis point to a conclusion that 4-APAA administered to rats either orally in drinking water or by topical administration to the colon substantially reduced intestinal inflammation as evidenced by reduced plasma extravasation, neutrophil infiltration, and preservation of normal histoarchitecture. In addition, APAZA™ compound reduced Toxin A induced colitis at concentrations 10-100 fold lower than that of sulfasalazine. Together these beneficial effects of APAZA™ compound and its components in these 3 models of colitis lead to a conclusion that APAZA™ is a useful agent in the treatment of colitis. Subsequent studies indicate synergistic effects of 5-ASA azo bonded to 4-APAA to form the APAZA™ compound.

Effects of Equimolar Rectal Doses of 5-ASA, 4-APAA and a Mixture of 5-ASA and 4-APAA on DNBS Colitis in the Rat The anti-inflammatory effects of equimolar rectal doses of 5-ASA and 4-APAA administered separately or as a mixture were evaluated in a DNBS model of colitis in rats.

The anti-inflammatory effects of 3 different treatments were compared in a DNBS model of colitis in 30 male Lewis rats weighing between 218 and 260 grams.

Animals were divided into 5 groups of 6 animals in each group:
0.7% methylcellulose (vehicle)+normal saline
0.7% methylcellulose (vehicle)+ethanolic solution of 2,4-dinitrobenzenesulfonic acid (DNBS) 30 mg
5-ASA at 100 mg/kg·day+DNBS 30 mg/rectally
4-APAA at 99 mg/kg·day+DNBS 30 mg/rectally
5-ASA+4-APAA mixture (APAZA™) at 199 mg/kg·day+DNBS 30 mg/rectally Experimental colitis was induced under light anesthesia (ketamine/xylazine) in 4 of 5 groups by instilling DNBS (30 mg) rectally at a volume of 0.5 mL to fasted rats. Each group of animals received rectal twice daily (bid) doses of either vehicle (0.7% methylcellulose) or test compounds (5-ASA, 4-APAA or APAZA™) for 4 days beginning 24 hours after either the normal saline or DNBS irritant was instilled. Body weight and incidence of diarrhea were recorded daily. Each animal in the 4 DNBS groups and in the single parallel saline group was sacrificed 5 days post irritant. Laparotomies and colectomies were performed and animals were scored for the presence and severity of intestinal adhesions, strictures, inflammation, and ulceration. Colon: body weight ratios were determined and tissue was examined histologically.

Severe inflammation was observed in all DNBS-treated groups as evidenced by intestinal adhesions, ulcerations, increased colon weight, tissue necrosis and clinical signs of weight loss and diarrhea. There were no statistical differences between groups in any of the observed parameters.

Net colon: body weight ratios were reduced by ~30% in all 3 active treatment groups (4-APAA, 5-ASA and 4-APAA+5-ASA mixture). Also, there were no differences observed in mean colonic wet: dry tissue weights for DNBS treated animals.

Comparison of vehicle to DNBS treatment, adhesion scores were reduced ~25%, 17%, and 38% in the 4-APAA, 5-ASA, and 5-ASA+4-APAA groups, respectively. In addition, the tissue necrosis scores were lower in the 5-ASA+4-APAA group due to spared areas in 2 of 4 animals relative to other DNBS animals receiving active treatment.

Rectal DNBS administration produced local colonic inflammation with segmental tissue destruction, thickening and adhesions. Trends toward improvement in all 3 treatment groups did not discriminate the effectiveness of 5-ASA+4-APAA mixture from individual components.

Effects of Equimolar Doses of APAZA™ and Sulfasalazine on DNBS Colitis in the Rat Study AA-PH-003 was designed to evaluate the anti-inflammatory efficacy of oral and rectal doses of APAZA™ and sulfasalazine in the DNBS colitis model in rats.

During this study the following compounds were administered: vehicle (0.7% methylcellulose, DNBS 30 mg, deionized water, APAZA™ 200 mg/kg·day and sulfasalazine 265.6 mg/kg·day.

Thirty-five adult male Lewis rats (body weight 200-250 g) were studied. Animals were divided into 7 groups with 5 animals in each group.

Vehicle (0.7% methyl cellulose)/rectally+normal saline/rectally
Vehicle/rectally+30 mg of DNB S/rectally
Vehicle/by oral (gavage)+30 mg DNBS/rectally
APAZA™ 200 mg/kg/rectally+30 mg DNBS/rectally
APAZA™ 200 mg/kg/by oral (gavage)+30 mg DNBS/rectally
Sulfasalazine 265.6 mg/kg/rectally+30 mg DNBS/rectally
Sulfasalazine 265.6 mg/kg/by oral (gavage)+30 mg DNBS/rectally Experimental colitis was induced in 6 of the 7 groups; and all 7 groups received either rectal or oral (gavage) bid doses of either vehicle or test compounds for the 4 days following induction of colitis. Animal body weights and incidence of diarrhea were recorded daily. Urine and feces were collected on days 1 and 3 for determination of APAZA™ and its metabolites (5-ASA, 4-APAA, 4-aceAPAA and 5-aceASA). Animals in the DNBS groups and the parallel deionized water group were sacrificed on day 5. Laparotomies and colectomies were performed and animals were scored for the presence and severity of intestinal adhesions, strictures, inflammation, and ulceration. Colon: body weight ratios were determined and colon histopathology was performed.

The following table provides a summary of the data used to determine the efficacy of oral and rectal doses of APAZA™ and sulfasalazine in a DNBS model of colitis in rats.

| Group | Net Colon: Body Weight Ratio | Colonic Inflammation Scores* | Mean Colon Length (cm) | Length of Colonic Inflammation (cm) | Average Diarrhea Score Day 3 | Mean Body Weight (g) | Colon Histopathology (# severe lesions) |
|---|---|---|---|---|---|---|---|
| Vehicle (0.7% methyl cellulose)/rectally + normal saline/rectally | Not done | 0 | 14.8 | 0 | 0 | 227.8 | Not done |

-continued

| Group | Net Colon: Body Weight Ratio | Colonic Inflammation Scores* | Mean Colon Length (cm) | Length of Colonic Inflammation (cm) | Average Diarrhea Score Day 3 | Mean Body Weight (g) | Colon Histopathology (# severe lesions) |
|---|---|---|---|---|---|---|---|
| Vehicle/rectally + 30 mg of DNBS | 0.2087 | 1.5 | 12.8 | 1.7 | 2 | 215.2 | Not done |
| Vehicle/orally + 30 mg DNBS | 0.3023 | 1.4 | 12.3 | 2.5 | 2.6 | 209.2 | 13 |
| APAZA ™ 200 mg/kg/ rectally + 30 mg DNBS | 0.1983 | 1.3 | 12.4 | 1.6 | 2 | 218.6 | Not done |
| APAZA ™ 200 mg/kg/ orally + 30 mg DNBS | 0.2309 | 1.4 | 12.3 | 2.5 | 2 | 213.8 | 2 |
| Sulfasalazine 265.6 mg/kg/ rectally + 30 mg DNBS | 0.179 | 1 | 12.8 | 1.8 | 2 | 217.0 | Not done |
| Sulfasalazine 265.6 mg/kg/ orally + 30 mg DNBS | 0.1862 | 1.4 | 12.9 | 2.3 | 2.4 | 215.4 | 8 |

*Colonic Inflammation Scoring Scale: 0 = no macroscopic inflammation; 1 = mild macroscopic evidence (minimal mucosal redness, edema) 2 = severe macroscopic evidence (pronounced mucosal redness, edema, and/or ulceration)

Based on the summary data provided in the foregoing table:

A 38.4% and 23.8% reduction relative to control in net colon: body weight (% BW) ratio was observed in the oral sulfasalazine and APAZA™ groups, respectively. No statistical significance between the groups was observed.

Colonic inflammation scores, mean colon lengths, length of colonic inflammation, average diarrhea scores and mean body weights were similar when the animals were treated orally with APAZA™, sulfasalazine or placebo.

While mucosal ulcer incidence was similar among all groups, ulcers were less severe in tissues from APAZA™-treated rats compared to tissues from placebo and sulfasalazine treated animals.

Minimal reduction in net colon: body weight (% BW) ratios, similar colonic inflammation scores, similar mean colon lengths, no difference in average diarrhea scores, and similar mean body weights were observed in the parallel rectal APAZA™ and sulfasalazine groups. No statistical significance for any of the defined efficacy parameters was observed.

Although equivocal, net colon: body weight (% BW) ratios and inflammation score results are indicative that oral and rectal APAZA™ and sulfasalazine had some activity in a DNBS model of colitis in rats. In addition, histological findings lead to a conclusion that APAZA™ reduces the severity of ulceration and subsequent fibrosis in DNBS colitis.

Effects of APAZA™ and Sulfasalazine on Dextran Sulfate Sodium Colitis in the Rat The effectiveness of APAZA™ and sulfasalazine in ameliorating intestinal inflammation in a model of dextran sulfate sodium (DSS) induced colitis in Sprague-Dawley rats was determined.

Thirty-six male Sprague-Dawley rats that were 7-8 weeks old and weighed 240-260 g were studied. Animals were divided into 6 groups with 6 animals in each group:

Placebo (0.7% methylcellulose) bid by oral (gavage), distilled water (DW) as drinking water
APAZA™ 100 mg/kg/bid by oral (gavage), DW as drinking water
Sulfasalazine 133 mg/kg/bid by oral (gavage), DW as drinking water
Placebo (0.7% methylcellulose) bid by oral (gavage), 5% DSS as drinking water
APAZA™ 100 mg/kg/bid by oral (gavage), 5% DSS as drinking water
Sulfasalazine 133 mg/kg/bid by oral (gavage), 5% DSS as drinking water Experimental colitis was induced by administering a 5% solution of DSS in drinking water for 10 days with a single control group of rats receiving DW only. One day prior to administration of DSS and continuing for a total of 11 consecutive days, each group of rats was treated twice daily with APAZA™, sulfasalazine, or placebo. After completion of the treatment period, rats were euthanized and the efficacy of the test drugs in inhibiting colitis was assessed by the following:

Disease Activity Index Scoring:

| Score | Weight Loss | Stool Consistency | Rectal Bleeding |
|---|---|---|---|
| 0 | None | Normal | None |
| 1 | 1-5% | | |
| 2 | 5-10% | Loose | Hemoccult+ |
| 3 | 10-20% | | |
| 4 | >20% | Diarrhea | Gross Bleeding |

Body weight
Colon wet weight: body weight ratios
Colonic Myeloperoxidase (MPO) activity
Histopathological changes of the colon In both APAZA™ and placebo treated rats drinking DSS, the DAI score was between 0-1, indicating a blunting of the symptoms (weight loss, diarrhea and rectal bleeding) associated with DSS colitis. In sulfasalazine treated rats drinking DSS the DAI score was significantly greater than the DAI score of sulfasalazine treated rats drinking DW on day 2 and at days 5-10, indicating an increase in the severity of the symptoms associated with DSS colitis.

All animals drinking DW gained weight over the 11 day treatment period while all of the rats drinking the DSS solution lost weight. However, the only statistically significant differences in body weights between rats drinking DW versus DSS were found in the sulfasalazine treated rats on days 10 and 11.

There was no statistically significant difference between the colon wet weight: body weight ratio in rats treated with APAZA™ and drinking either DW or DSS. The colon wet weight:body weight ratios in rats drinking DSS and treated with sulfasalazine or placebo were increased when compared to rats drinking DW.

Myeloperoxidase (MPO) is an enzyme marker useful in quantifying the degree of inflammation and in estimating the infiltration of neutrophils in tissue. Colonic MPO activity was similar following oral administration of APAZA™ or placebo to rats receiving DSS, in the sulfasalazine treated rats drinking DSS a significant increase in tissue MPO activity was observed. This biochemical finding confirms the histological observation of heavy infiltration of inflammatory cells, including neutrophils, in the colons of rats drinking DSS and treated with sulfasalazine.

Figure 5:
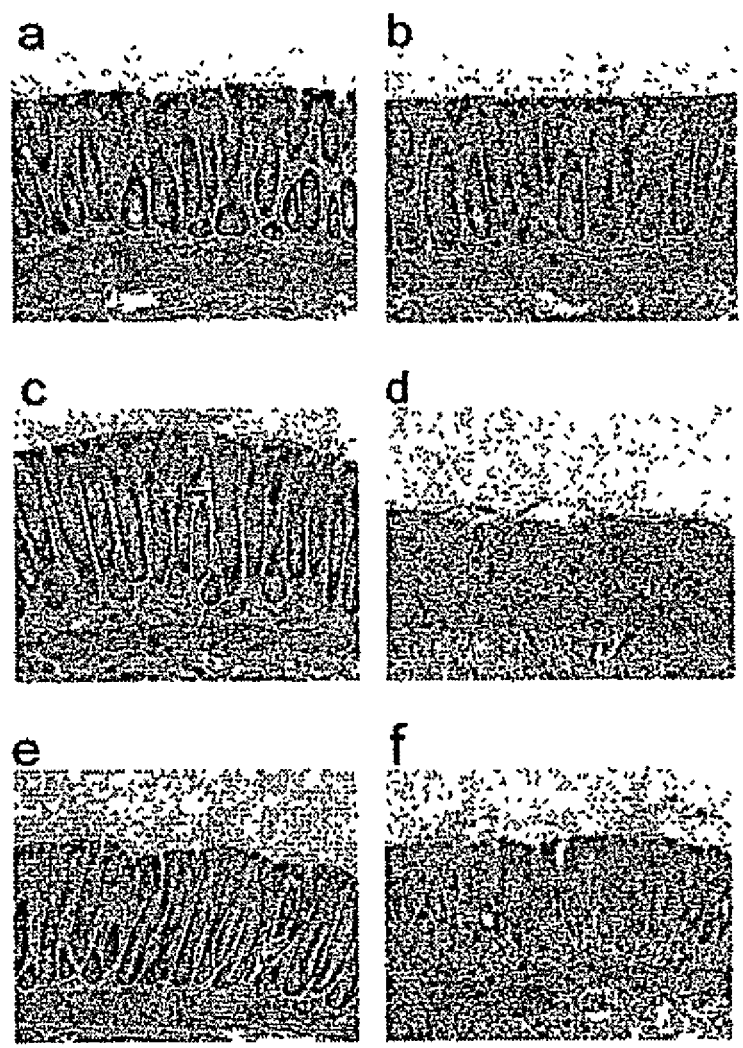
FIGS. 5 A-F show histological changes in animals, following administration of APAZA™ compound, sulfasalazine and placebo treatments in animals receiving dextran sulfate sodium (DSS) versus distilled water.

Histological changes in animals, following administration of APAZA™, sulfasalazine and placebo treatments, were evaluated in animals receiving DSS versus DW, as shown in FIG. 5. DSS caused severe colitis with loss of crypts, vascular edema, and heavy infiltration of inflammatory cells in rats treated with placebo (f) or sulfasalazine (d). Rats treated with placebo had less colonic damage than those receiving sulfasalazine but still had some crypt shortening and mucosal inflammatory cell infiltration. In contrast, DSS rats treated with APAZA™ (b) were largely protected from the tissue damaging effects of DSS with the colonic histology being nearly normal.

In conclusion, APAZA™ inhibited DSS-induced colitis more effectively than sulfasalazine or placebo in terms of lower DAI scores (fewer observed symptoms associated with colitis), prevention of increased colon wet weight: body weight ratio, a decrease in MPO activity, and preservation of normal histological structure. Surprising results in the sulfasalazine/DSS treated animals could not be explained by any specific methodological mistakes during the conduct of the experiment.

Oral Administration of 4-APAA Dimer Inhibition of Toxin A-Induced Colitis in Anesthetized Rats Eighteen adult male Sprague-Dawley rats, weighing 175-225 grams, were divided into 3 groups, each consisting of 6 animals:

4-APAA dimer (AA-013) 100 mg/kg day orally+Toxin A (10 µg) injected into the lumen of the colon Vehicle (DW) orally+Toxin A (10 µg) injected into the lumen of the colon Vehicle (DW) orally Following 5 days of 4-APAA dimer administration in drinking water, both ketamine (67 mg/kg) and xylazine (33 mg/kg) were administered, an isolated colonic segment was surgically created, and 10 µg of *Clostridium difficile* toxin A was injected into the lumen of the colon. After 3 hours, the rats were euthanized and colonic inflammation was assessed by quantitating luminal fluid accumulation and myeloperoxidase (MPO) content in the colon tissue. In addition, histological evaluation of the treated colon segments was completed.

Figure 6:
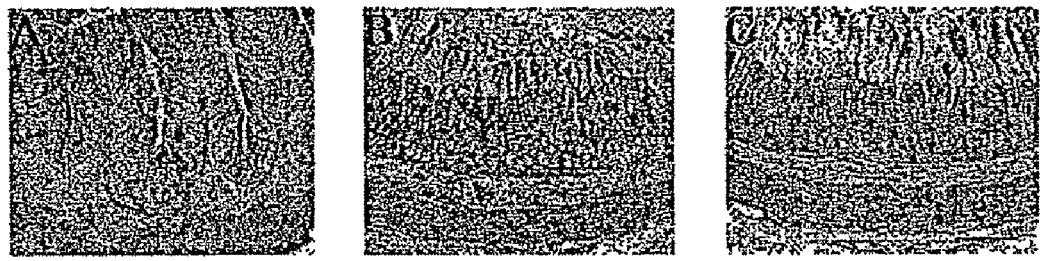
FIGS. 6 A-C display colon sections showing the effects of chronic treatment with 4-APAA dimer on toxin A-induced structural damage of the colon. H&E-stained sections of rat colon were prepared after the rats were treated for five days with drinking water containing vehicle (DW; A), vehicle followed on the fifth day with acute treatment with 10 µg toxin A (B), or 100 mg/kg·day 4-APAA followed on the fifth day with acute treatment with 10 µg toxin A (C). Scale bar=100 µm.

The effects of chronic treatment with 4-APAA on toxin A-induced colitis were assessed by luminal fluid accumulation and tissue MPO content. The response to 4-APAA dimer was compared on the basis of percent inhibition of the responses to toxin A alone. 4-APAA dimer inhibited 21±8% of the toxin A induced luminal fluid accumulation and 60±9% of toxin A induced MPO activity The effects of chronic treatment with 4-APAA dimer on toxin A induced structural damage of the colon is shown in FIG. 6. Toxin A caused widespread damage to the structural integrity of the colon (loss of folding of the mucosa, ulceration of the epithelial surface, loss of goblet cells, and infiltration of immune system cells). Chronic treatment with oral 4-APAA dimer (mg/kg·day) partially inhibited colonic inflammation induced following an injection of toxin A into the colon of rats. 4-APAA dimer significantly inhibited toxin A induced MPO activity but did not inhibit either the structural damage or the luminal fluid accumulation caused by toxin A.

Chronic Oral Administration of 4-APAA Inhibition of Toxin A-Induced Colitis in Anesthetized Rats Eighteen adult male Sprague-Dawley rats weighing 175-222 grams were divided into 3 groups each consisting of 6 animals:

4-APAA (AA-002) 100 mg/kg orally+Toxin A (10 µg) injected into the lumen of the colon Vehicle (DW) orally+Toxin A (10 µg) injected into the lumen of the colon Vehicle (DW) orally Following 5 days of 4-APAA administration in drinking water, both ketamine (67 mg/kg) and xylazine (33 mg/kg) were administered, an isolated colonic segment was surgically created, and 10 µg of *Clostridium difficile* toxin A was injected into the lumen of the colon. After 3 hours, the rats were euthanized and colonic inflammation was assessed by quantitating luminal fluid accumulation and myeloperoxidase (MPO) content in the colon tissue. In addition, histological evaluation of the treated colon segments was completed.

The effects of chronic treatment with 4-APAA on toxin A-induced colitis were assessed by luminal fluid accumulation and tissue MPO content. Chronic oral administration of 4-APAA before toxin A administration significantly inhibited both toxin A-induced luminal fluid accumulation and MPO activity. The responses to 4-APAA were compared on the basis of the percent of inhibition compared to the response to toxin A alone. Toxin A luminal fluid accumulation was inhibited 84±6% and MPO activity was reduced by 89±8% following administration of 4-APAA.

Figure 7:
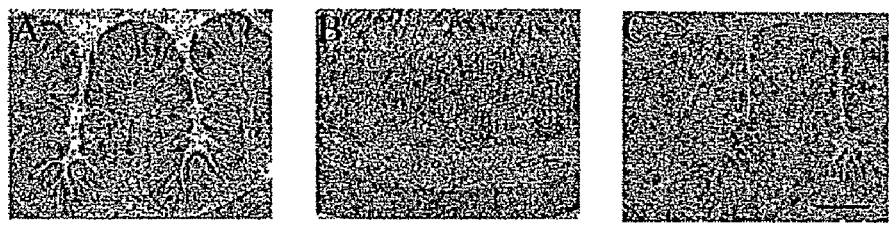
FIGS. 7 A-C display colon sections showing the effects of chronic treatment with 4-APAA on the toxin A-induced structural damage of the colon. H&E-stained sections of rat colon were prepared after the rats were treated for five days with drinking water containing vehicle (DW; A), vehicle (DW) followed on the fifth day with acute treatment with 10 µg toxin A (B), or 100 mg/kg·day 4-APAA followed on the fifth day with acute treatment with 10 µg toxin A (C). Scale bar=100 µm.

The effects of chronic treatment with 4-APAA on the toxin A-induced structural damage of the colon was assessed histologically, as shown in FIG. 7. It can be seen that toxin A causes widespread damage to the structural integrity of the of colon including loss of folding of the mucosa, ulceration of the epithelial surface, loss of goblet cells, and infiltration of immune system cells, including neutrophils. Oral administration of 4-APAA over 5 days, protected the structural integrity of the colon against the damaging effects of toxin A.

Results from Part 2 of this study are indicative that treatment with 4-APAA is an effective inhibitor of toxin A induced acute colonic inflammation in Sprague-Dawley rats.

Inhibition of *Clostridium difficile* Toxin A-Induced Colitis in Rats by APAZA™ and 4-APAA The APAZA™ compound [molecule of 5-aminosalicylic acid (5-ASA) linked to one molecule of 4-aminophenylacetic acid (4-APAA) by an azo bond] was tested for its ability to inhibit acute colitis in rats caused by *Clostridium difficile* toxin A. When administered chronically for 5 days in drinking water, APAZA™ significantly inhibited toxin A-induced myeloperoxidase (MPO) activity, luminal fluid accumulation, and structural damage to the colon at doses from 1-100 mg/kg·day. For comparison, sulfasalazine was administered in identical doses and was found to significantly inhibit toxin A-induced colitis only at the dose of 100 mg/kg·day. When 4-APAA alone was administered chronically in drinking water, it also inhibited toxin A-induced colonic inflammation at a dose of 100 mg/kg·day. In order to determine if 4-APAA has a direct anti-inflammatory effect on the colon rather than a systemic effect, 4-APAA was administered acutely to surgically prepared isolated colonic segments by intraluminal injection in anesthetized rats 30 minutes before toxin A was injected. 4-APAA strongly and significantly inhibited toxin A-induced colitis in this experiment at doses as low as 10 μg/segment. It is concluded that APAZA™ is a potent inhibitor of toxin A-induced colonic inflammation in rats and that its constituent, 4-APAA, is responsible for this increased protection against colitis compared to the 5-ASA component of sulfasalazine.

Materials. Sulfasalazine and 4-APAA were purchased from Sigma-Aldrich (St. Louis, Mo.). Toxin A was purchased from TechLab, Inc. (Blacksburg, Va.). APAZA™ was synthesized as described in U.S. Pat. No. 6,583,128. Rats were purchased from Charles River Laboratories, Inc. (Wilmington, Mass.).

Drug Administration. In studies using chronic administration, sulfasalazine, APAZA™, and 4-APAA were administered in the drinking water at doses ranging from 0.1-100 mg/kg·d for 5 days. Sulfasalazine and APAZA™ were initially dissolved in 0.1 N NaOH at 30 times the desired final concentration and then the pH was adjusted to 8.5 with 1 N HCl and the solution was diluted 30-fold with distilled water. 4-APAA was dissolved in water. On the fifth day, the rats were fasted overnight (with access to their drinking water±sulfasalazine, APAZA™, or 4-APAA ad lib), anesthetized, and isolated colonic segments were surgically created as described below. In studies using acute administration, the rats were pretreated by injection of 4-APAA at doses of 10 or 100 μg in 200 μl of PBS (pH 7.4) into the lumen of the colonic segment using a 27 ga syringe needle. Toxin A (10 μg) in 200 μl of PBS (pH 7.4) was tested alone or injected into the lumen of the colonic segment 30 minutes after 4-APAA using a 27 ga syringe needle.

Surgery. Isolated colonic segments were created in male Sprague-Dawley rats (150-175 g) as described previously for isolated ileal segments (see, *Gastroenterol.* 111: 1272-1280 (1996) and *Proc. Natl. Acad. Sci. USA* 91: 947-951 (1994). Rats fasted overnight with free access to drinking water were anesthetized by intramuscular injection of 67 mg/kg ketamine:33 mg/kg xylazine. A midline abdominal incision was made and colonic segments 5 cm in length were created by ligation with 4-0 silk sutures, taking care not to disturb the vascular supply. Toxin A (10 μg) in 400 μl of PBS (pH 7.4) was injected into the lumen of the colonic segment using a 27 ga syringe needle. Control rats were prepared similarly and their colonic segments were injected with the vehicles. The midline incision was then closed with a running suture, and the rats were placed on a heating pad at 37° C. for 3 hours. After 3 hours, the rats were euthanized and samples of the treated colonic segments were taken for analysis in vitro.

Histopathology. The severity of colonic histological damage was assessed using formalin-fixed, paraffin-embedded, H&E-stained sections.

Luminal Fluid Accumulation. Luminal fluid accumulation was measured gravimetrically. After 3 hours of treatment, the isolated colonic segments were removed, weighed, and their lengths were measured. Luminal fluid accumulation is expressed as mg wet weight per cm length.

Myeloperoxidase Activity. Myeloperoxidase (MPO) activity was measured as described previously (see, *J. Invest. Dermatol.* 78: 206-209 (1982)). Briefly, pieces of control and treated colonic segments were homogenized in 0.5% hexadecyltrimethylammonium bromide in 50 mM $KH_2PO_4$ (pH 6), freeze/thawed three times, centrifuged at 4° C. for 2 minutes, and then the absorbance of each supernatant was read at 460 nm at 0, 30, and 60 seconds after the addition of 2.9 ml of o-dianisidine dihydrochloride to 0.1 ml supernatant. The maximal change in absorbance per minute was used to calculate the units of MPO activity based on the molar absorbency index of oxidized o-dianisidine of $1.13 \times 10^4 \, M^{-1} \, cm^{-1}$. The results are expressed as MPO units of activity per mg of tissue wet weight.

Statistical Analysis. Results are expressed as mean±SEM. Differences among groups of three or more were examined by one-way ANOVA with the Tukey-Kramer post test. Differences between the means of two groups were analyzed by unpaired t test. P<0.05 was considered significant. All tests were performed using GraphPad Instat, version 3.05 for Windows (GraphPad Software, San Diego, Calif.).

Figure 8:
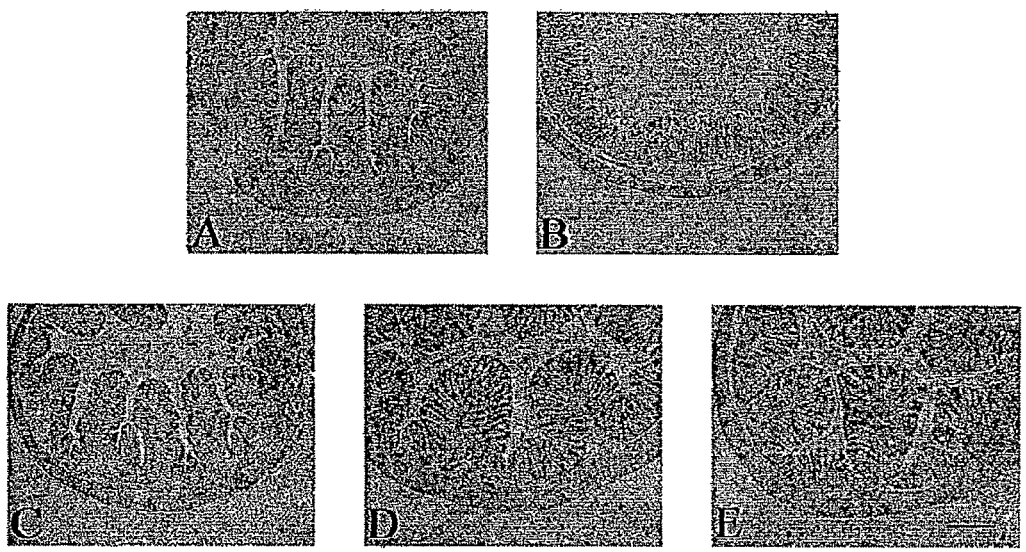
FIGS. 8 A-E illustrate the effects of chronic treatment with APAZA™ on toxin A-induced structural damage of the colon as assessed by H&E staining of fixed tissue.

Results. The effects of chronic treatment with APAZA™ on toxin A-induced structural damage of the colon as assessed by H&E staining of fixed tissue is shown in FIG. 8. APAZA™ administered in the drinking water at all three doses (1, 10, and 100 mg/kg·day) strongly protected the structural integrity of the rat colon against the damaging effects of toxin A. The degree of protection afforded by APAZA™ appeared to be virtually complete at all three doses so there was little evidence of a dose-related effect. In addition, there was little variability among the several histological preparations for the effects of APAZA™ unlike what was observed for the highest dose of sulfasalazine described below.

Figure 9:
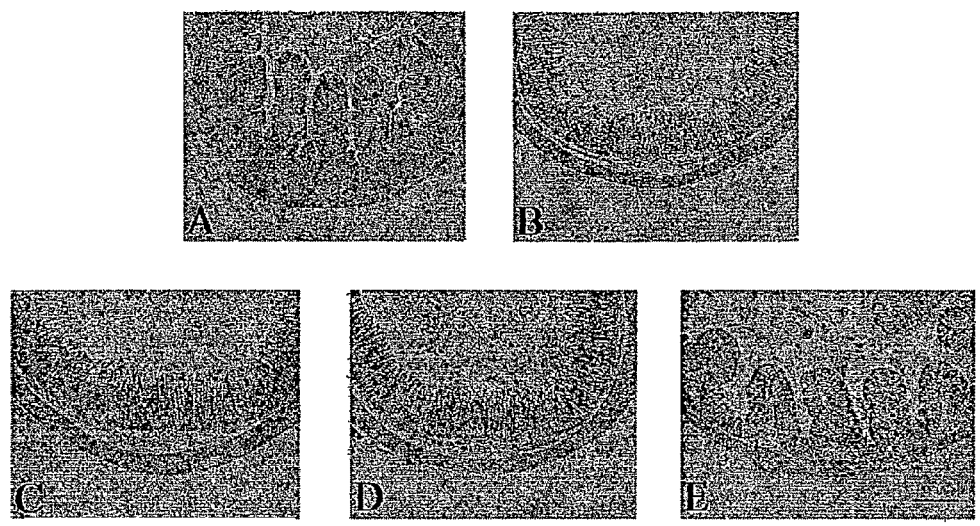
FIGS. 9 A-E illustrate the effects of chronic treatment with sulfasalazine on toxin A-induced structural damage of the colon as assessed by H&E staining of fixed tissue.

The effects of sulfasalazine on toxin A-induced colitis in rats was also assessed. Sulfasalazine is a well-established inhibitor of chronic intestinal inflammation and so it was useful to establish its potency and efficacy in the rat toxin A acute colitis model in order to assess the relative effects of APAZA™. The effects of chronic treatment with sulfasalazine on toxin A-induced structural damage of the colon as assessed by H&E staining of fixed tissue is shown in FIG. 9. Toxin A causes widespread damage to the structural integrity of the rat colon. Most noticeable is the loss of folding of the mucosa, which can be a function of the smooth muscle of the muscularis mucosa. In addition, toxin A appears to cause ulceration of the epithelial surface, loss of goblet cells, and infiltration of immune system cells, including neutrophils. Sulfasalazine administered in the drinking water at doses of 1 and 10 mg/kg·day had little effect on the structural integrity of the rat colon against the damaging effects of toxin A. FIG. 9 shows that sulfasalazine at these doses did not prevent the loss of mucosal folding, the loss of goblet cells, or the infiltration of immune system cells caused by toxin A. However, at the dose of 100 mg/kg·day sulfasalazine did inhibit toxin A-induced histological damage (FIG. 9, panel E). Interestingly, there appeared to be significant variability in the histological protection provided by sulfasalazine at the dose of 100 mg/kg·day.

Figure 10:
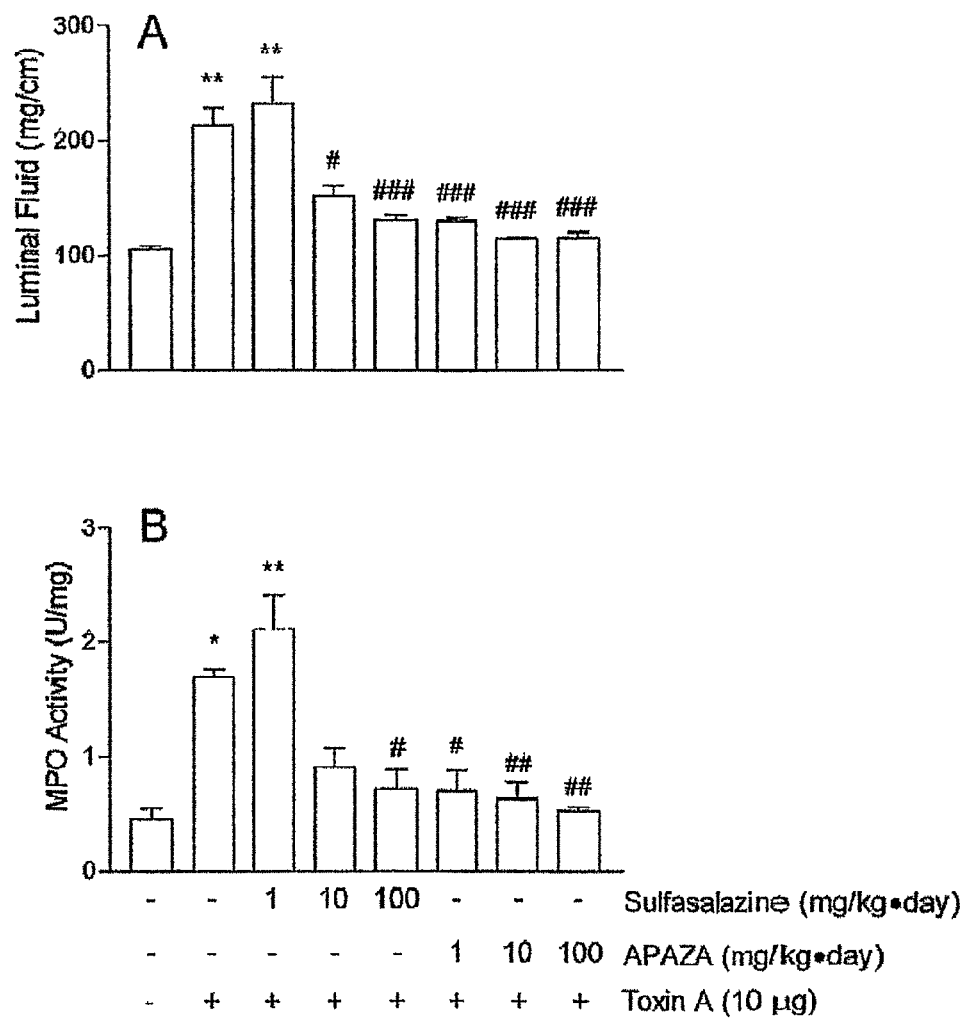
FIGS. 10 A-B illustrate the effects of chronic treatment with three doses each of sulfasalazine and APAZA™ on toxin A-induced colitis as assessed by luminal fluid accumulation and tissue MPO content.

The effects of chronic treatment with three doses each of sulfasalazine and APAZA™ on toxin A-induced colitis as assessed by luminal fluid accumulation and tissue MPO content are shown in FIG. 10. Toxin A strongly stimulated luminal fluid accumulation and MPO activity in the rat colon. Chronic treatment of the rats with 1 mg/kg·day of sulfasalazine before toxin A administration did not significantly inhibit toxin A-induced luminal fluid accumulation or toxin A-induced MPO activity. At a dose of 10 mg/kg·day, sulfasalazine significantly inhibited toxin A-induced luminal fluid accumulation but not toxin A-stimulated MPO activity. At the dose of 100 mg/kg·day, sulfasalazine significantly inhibited both luminal fluid accumulation and MPO activity induced by toxin A. In contrast, chronic treatment with APAZA™ significantly inhibited toxin A-induced luminal fluid accumulation and MPO activity at all three doses tested (1, 10, and 100 mg/kg·day). The degree of inhibition by the lowest dose of APAZA™ tested, 1 mg/kg·day, was equivalent to the degree of inhibition observed in response to the highest dose of sulfasalazine tested, 100 mg/kg·day.

Figure 11:
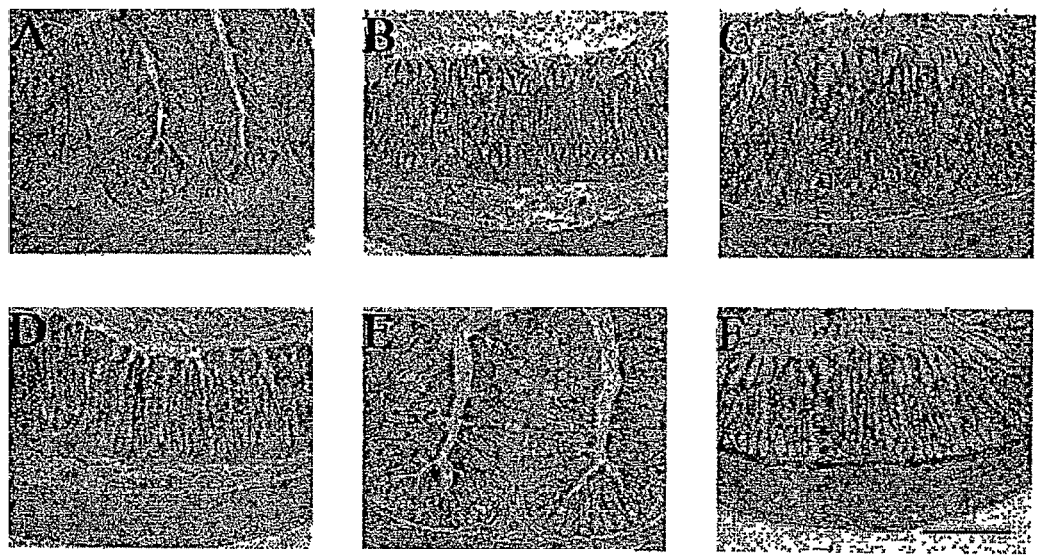
FIGS. 11 A-F illustrate the strong protective effects of APAZA™ administered in the drinking water for five days on the structural integrity of the rat colon against the damaging effects of toxin A at the dose of 1 mg/kg·day.

To determine the potency of APAZA™ for inhibition of toxin A-induced colitis in rats, an additional study was performed using lower doses of APAZA™. As shown in FIG. 11, APAZA™ administered in the drinking water for 5 days strongly protected the structural integrity of the rat colon against the damaging effects of toxin A at the dose of 1 mg/kg day, confirming the previous result. At the dose of 0.5 mg/kg·day, APAZA™ partially protected the structural integrity of the rat colon against toxin A. At this dose, APAZA™ appeared to provide nearly complete protection against surface mucosal ulceration but not against the toxin A-induced loss of mucosal folding or immune cell infiltration. APAZA™ appeared to have little if any protective effect against the structurally damaging effects of toxin A at the dose of 0.1 mg/kg·day. Thus, the complete dose-response curve for APAZA™ for inhibiting colitis in this model appeared to occur between doses of 0.1 and 1 mg/kg·day. Sulfasalazine at a dose of 1 mg/kg·day had little effect on toxin A colitis, confirming the previous result.

Figure 12:
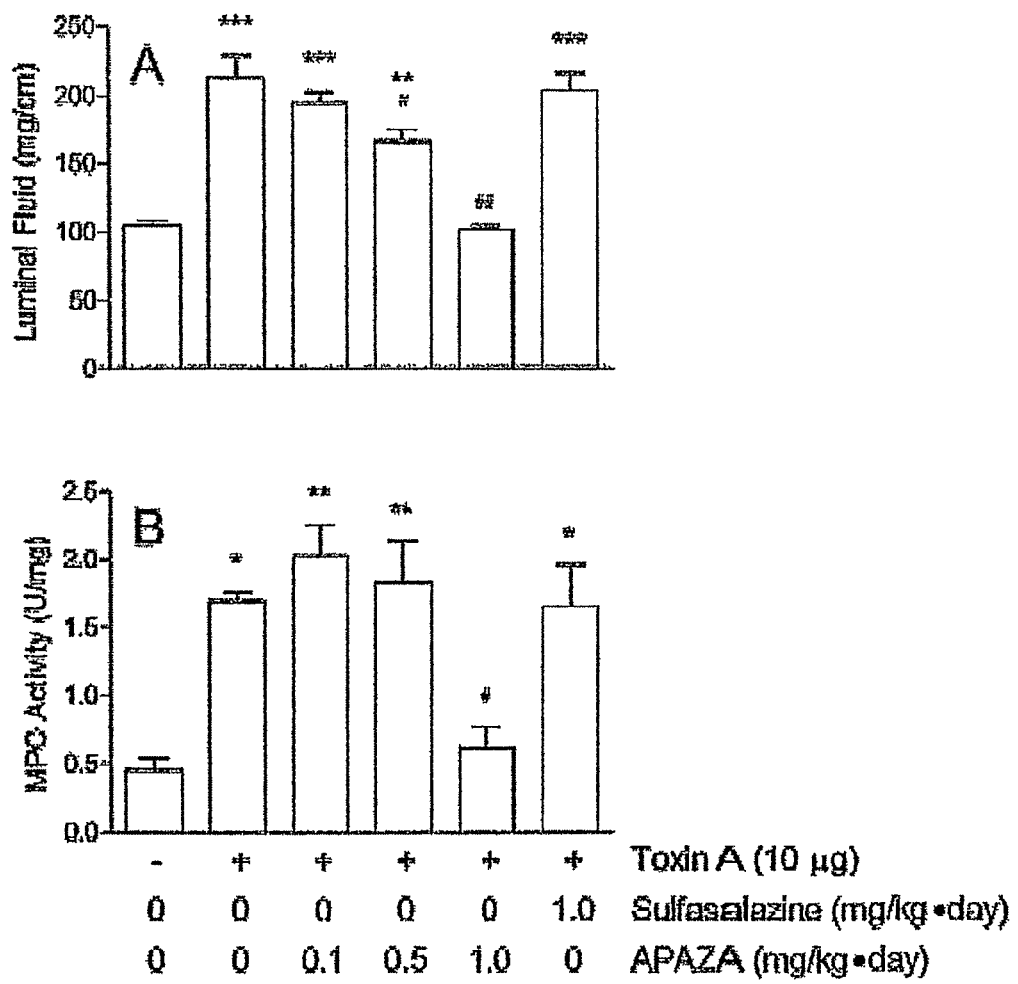
FIGS. 12 A-B illustrate the effects of chronic treatment with APAZA™ at these lower doses on toxin A-induced colitis as assessed by luminal fluid accumulation and tissue MPO content.

The effects of chronic treatment with APAZA™ at these lower doses on toxin A-induced colitis as assessed by luminal fluid accumulation and tissue MPO content are shown in FIG. 12. Chronic treatment of the rats with 1 mg/kg·day of sulfasalazine did not significantly inhibit toxin A-induced luminal fluid accumulation or toxin A-induced MPO activity, as before. In contrast, chronic treatment with APAZA™ significantly inhibited toxin A-induced luminal fluid accumulation at the doses of 0.5 and 1 mg/kg·day and MPO activity at 1 mg/kg·day. Thus, APAZA™ appeared to be at least 10-20-fold more potent than sulfasalazine in these actions. The potency of APAZA™ for inhibition of toxin A-induced luminal fluid accumulation and MPO activity closely matched its potency for inhibition of toxin A-induced structural damage.

Figure 13:
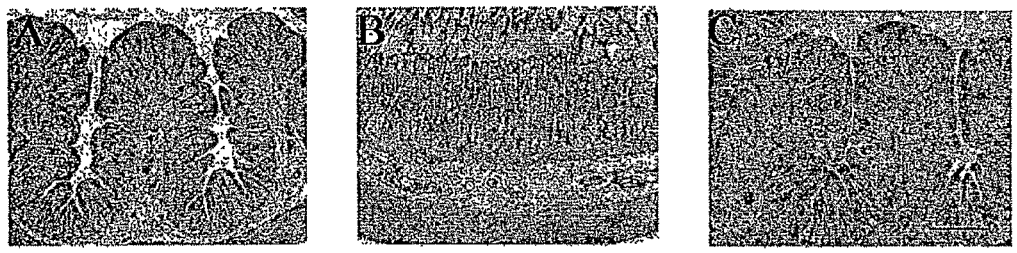
FIGS. 13 A-C illustrate the effects of chronic treatment with 4-APAA at the dose of 100 mg/kg·day on toxin A-induced structural damage of the colon as assessed by H&E staining of fixed tissue.

Chronic administration of 4-APAA alone in the drinking water was performed in order to determine if the 4-APAA moiety of APAZA™ by itself inhibits toxin A colitis. The effects of chronic treatment with 4-APAA at the dose of 100 mg/kg-d on toxin A-induced structural damage of the colon as assessed by H&E staining of fixed tissue is shown in FIG. 13. 4-APAA administered in the drinking water strongly protected the structural integrity of the rat colon against the damaging effects of toxin A. FIG. 13 shows that normal mucosal folding is preserved when the rats are treated chronically with 4-APAA before toxin A administration. In addition, 4-APAA strongly inhibited toxin A-induced epithelial surface ulceration, preserved goblet cells, and inhibited immune cell infiltration into the colon.

Figure 14:
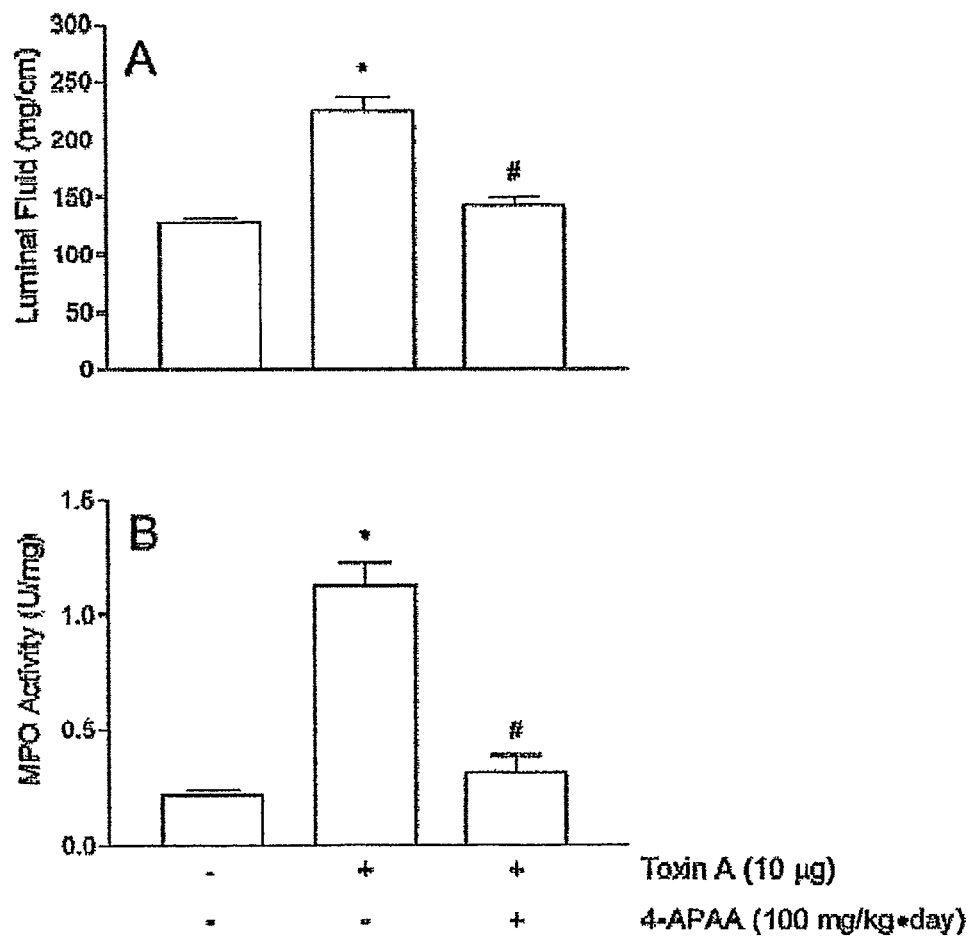
FIGS. 14 A-B illustrate the effects of chronic treatment with 4-APAA on toxin A-induced colitis as assessed by luminal fluid accumulation and tissue MPO content.

The effects of chronic treatment with 4-APAA on toxin A-induced colitis as assessed by luminal fluid accumulation and tissue MPO content are shown in FIG. 14. Chronic treatment of the rats with 4-APAA before toxin A administration significantly inhibited both toxin A-induced luminal fluid accumulation and MPO activity. The luminal fluid and MPO responses to 4-APAA were compared on the basis of percent inhibition of the responses to toxin A alone. 4-APAA inhibited 84±6% of toxin A-induced luminal fluid accumulation and 89±8% of toxin A-induced MPO activity (P=0.63). Thus, 4-APAA inhibited these two indices of colonic inflammation equally.

Figure 15:
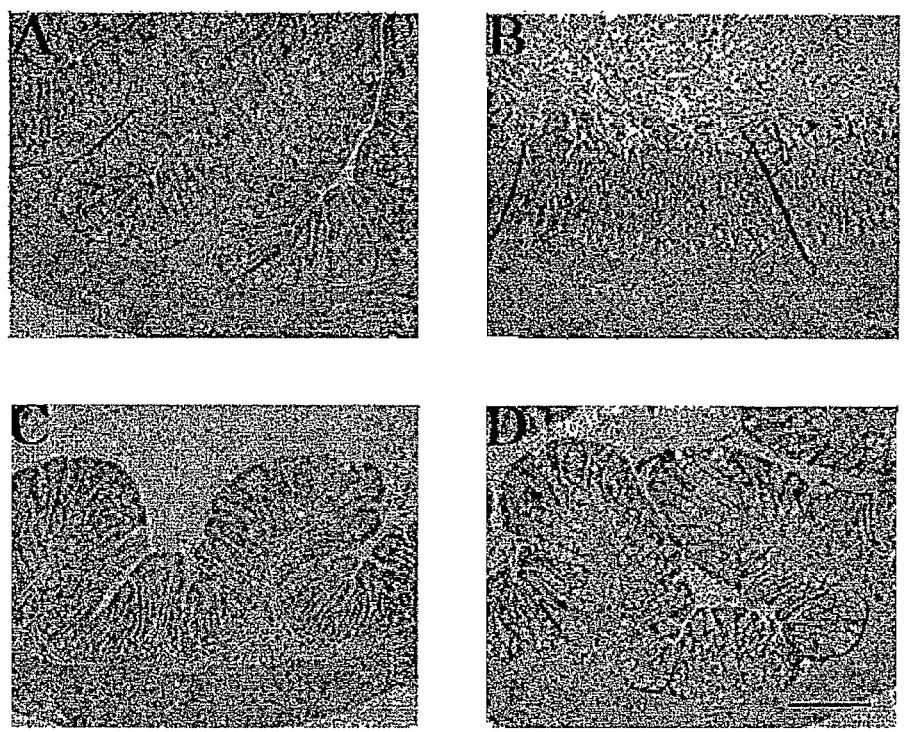
FIGS. 15 A-D illustrate the effects of acute pretreatment with 4-APAA on toxin A-induced structural damage of the colon as assessed by H&E staining of fixed tissue.

Acute treatment of the colon by injecting 4-APAA intraluminally 30 minutes before toxin A administration was used to determine if 4-APAA inhibits toxin A colitis topically in the colon at very low doses. The effects of acute pretreatment with 4-APAA on toxin A-induced structural damage of the colon as assessed by H&E staining of fixed tissue is shown in FIG. 15. 4-APAA at both 10 and 100 μg doses strongly protected the structural integrity of the rat colon against the damaging effects of toxin A. FIG. 15 shows that normal mucosal folding is preserved when the colon is pretreated for 30 minutes with 4-APAA before toxin A administration. In addition, 4-APAA strongly inhibited toxin A-induced epithelial surface ulceration, preserved goblet cells, and inhibited immune cell infiltration into the colon. The dose of 100 μg 4-APAA appeared to inhibit the inflammatory effects of toxin A slightly better than the dose of 10 μg 4-APAA.

Figure 16:
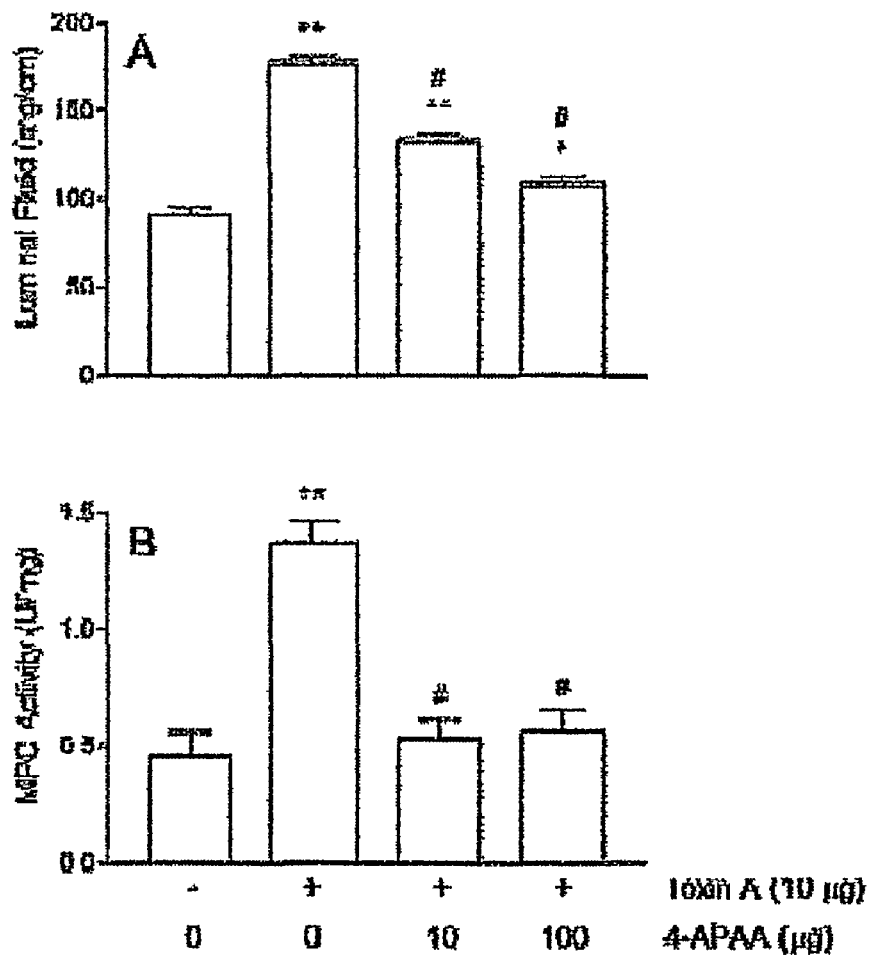
FIGS. 16 A-B illustrate the effects of acute pretreatment with 4-APAA on toxin A-induced colitis as assessed by luminal fluid accumulation and tissue MPO content.

The effects of acute pretreatment with 4-APAA on toxin A-induced colitis as assessed by luminal fluid accumulation and tissue MPO content are shown in FIG. 16. Pretreatment of the colon with 10 or 100 μg of 4-APAA 30 minutes before toxin A administration significantly inhibited both toxin A-induced luminal fluid accumulation and MPO activity. The 4-APAA inhibition of luminal fluid accumulation was partial but the inhibition of MPO activity was nearly complete. The dose of 100 μg 4-APAA was more effective than the dose of 10 μg in inhibiting luminal fluid accumulation, but the two doses inhibited MPO activity similarly. The responses to the two doses of 4-APAA were compared on the basis of percent inhibition of the responses to toxin A alone. For inhibition of toxin A-induced luminal fluid accumulation, 100 μg of 4-APAA was significantly more potent than 10 μg (80±5% inhibition vs. 52±4% inhibition; P<0.001). However, the MPO responses to the two doses of 4-APAA were not significantly different (91±8% inhibition for 10 μg dose and 89±10% inhibition for 100 μg dose; P=0.87).

The main findings of the present study are that 4-APAA alone and APAZA™ (5-ASA+4-APAA) are effective inhibitors of experimental colitis in a rat model and that APAZA™ is more potent than sulfasalazine. This is also apparently the first demonstration that sulfasalazine strongly inhibits *Clostridium difficile* toxin A-induced colitis in rats. After demonstrating that oral administration of sulfasalazine over 5 days in the drinking water significantly inhibited all indices of colon inflammation, it was shown that lower doses of APAZA™ administered identically were equally effective. To demonstrate that the 4-APAA moiety of APAZA™ was responsible for the increased potency of APAZA™ over sulfasalazine, it was shown that 4-APAA alone administered chronically in the drinking water in the same way also significantly inhibited experimental toxin A-induced colitis in rats. This result demonstrates that systemic distribution of 4-APAA can inhibit colitis because it is likely that orally administered 4-APAA is absorbed into the body in the small intestine. Finally, this study shows that the inflammation-inhibiting activity of 4-APAA also occurs by a local topical effect in the colon by demonstrating that acute injection of very small doses of 4-APAA directly into the lumen of surgically isolated colonic segments 30 minutes before administering toxin A also strongly inhibited colitis. As little as 10 μg of 4-APAA tested in this manner was effective.

The increased potency of APAZA™ versus sulfasalazine can be due to the inclusion of two different active moieties in APAZA™, 5-ASA and 4-APAA, versus sulfasalazine, which only contains 5-ASA as an active ingredient. Dose-response studies showed that APAZA™ was approximately 10-20 times more potent than sulfasalazine in inhibiting toxin A-induced colitis in rats. This difference in potency could be explained if 5-ASA and 4-APAA inhibit intestinal inflammation by different mechanisms and have synergistic effects when administered together in a compound such as APAZA™.

Relative Potencies of 4-APAA Versus 5-ASA for Inhibition of Toxin A-Induced Colitis in Rats.

Adult male Sprague-Dawley rats (175-225 grams body weight) were purchased from Charles River Labs (Raleigh, N.C.). 4-APAA and 5-ASA were separately injected into the lumen of an isolated segment of the rat colon at doses of 0.01, 0.1, 1, and 10 µg (in volumes of 200 µl) 30 minutes prior to injection of 10 µg of *Clostridium difficile* toxin A. In a follow-up study, a combined dose of 10 ng (0.01 µg) each of 4-APAA and 5-ASA was injected prior to toxin A.

Duration of dosing was five days. Colonic inflammation was assessed by quantitating luminal fluid accumulation and myeloperoxidase content in the colonic segment tissue, and by examination of colonic structural damage using hematoxylin & eosin-stained sections of the treated colonic segment.

Surgery. Rats fasted overnight with free access to water were anesthetized by an injection of 67 mg/kg ketamine:33 mg/kg xylazine. A midline abdominal incision was made and colonic segments 5 cm in length were constructed by ligation with 4-0 silk sutures, taking care not to disturb the vascular supply. The rats were pretreated by injection of 4-APAA or 5-ASA at doses of 0.01, 0.1, 1, or 10 µg, or a combined dose of 4-APAA plus 5-ASA at 0.01 µg each, in 200 µl of PBS (pH 7.4) into the lumen of the colonic segment using a 27 ga syringe needle. Toxin A (10 µg) in 200 µl of PBS (pH 7.4) was injected into the lumen of the colonic segment 30 minutes after 4-APAA or 5-ASA using a 27 ga syringe needle. The midline incision was then closed with a running suture, and the rats were placed on a heating pad at 37° C. for 3 hours.

Luminal Fluid Accumulation. Luminal fluid accumulation was measured gravimetrically. After 3 hours of treatment, the isolated colonic segments were removed, weighed, and their lengths were measured. Luminal fluid accumulation is expressed as mg wet weight per cm length.

Myeloperoxidase Activity. Pieces of control and treated colonic segments were homogenized in 0.5% hexadecyltrimethylammonium bromide in 50 mM $KH_2PO_4$ (pH 6), freeze/thawed three times, centrifuged at 4° C. for 2 minutes, and then the absorbance of each supernatant was read at 460 nm at 0, 30, and 60 seconds after the addition of 2.9 ml of o-dianisidine dihydrochloride to 0.1 ml supernatant. The maximal change in absorbance per minute was used to calculate the units of MPO activity based on the molar absorbency index of oxidized o-dianisidine of $1.13\times10^4$ $M^{-1}$ $cm^{-1}$. The results are expressed as MPO units of activity per mg of tissue wet weight.

Histology. The severity of mucosal histological damage was assessed using formalin-fixed, paraffin-embedded, H&E-stained sections.

Statistical Methods. Results are expressed as mean±SEM. Differences among groups were examined by one-way ANOVA with the Tukey-Kramer post test. P<0.05 was considered significant. All tests were performed using GraphPad Instat, version 3.05 for Windows (GraphPad Software, San Diego, Calif.).

Figure 17:
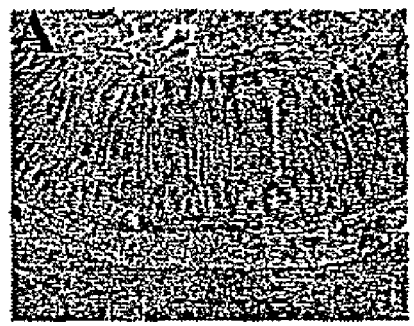
FIGS. 17 A-D illustrate the effects of toxin A on colon histology and inhibition of these effects by treatment with 4-APAA at four doses. H&E-stained sections of rat colon were prepared after the rats were treated for three hours with toxin A (10 µg) after a 30 minute pretreatment with 4-APAA. (A) Pretreatment with 0.01 µg 4-APAA. (B) Pretreatment with 0.1 µg 4-APAA. (C) Pretreatment with 1.0 µg 4-APAA. (D) Pretreatment with 10 µg 4-APAA. Scale bar=100 µm.
Figure 17:
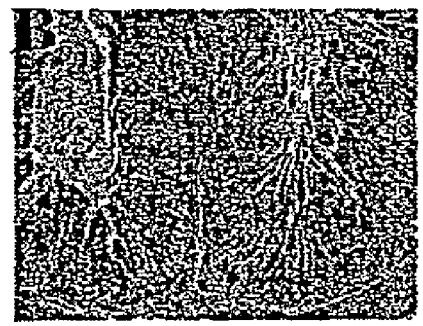
Figure 17:
Figure 17:

The effects of acute treatment with 4-APAA at several doses on toxin A-induced structural damage of the colon as assessed by H&E staining of fixed tissue is shown in FIG. 17. It can be seen that 4-APAA at the dose of 0.01 µg did not prevent the loss of mucosal folding, surface ulceration, loss of goblet cells, or infiltration of immune system cells caused by toxin A. There was a correlation between increased protection of the colon and increasing dose of 4-APAA such that 4-APAA at doses of 0.1 and 1.0 µg preserved mucosal folding (FIGS. 17B & C) and surface ulceration was also largely absent at the 4-APAA dose of 1.0 µg (FIG. 17C). At the 4-APAA dose of 10 µg, the colon was virtually completely protected against the structural damage caused by toxin A (FIG. 17D).

Figure 18:
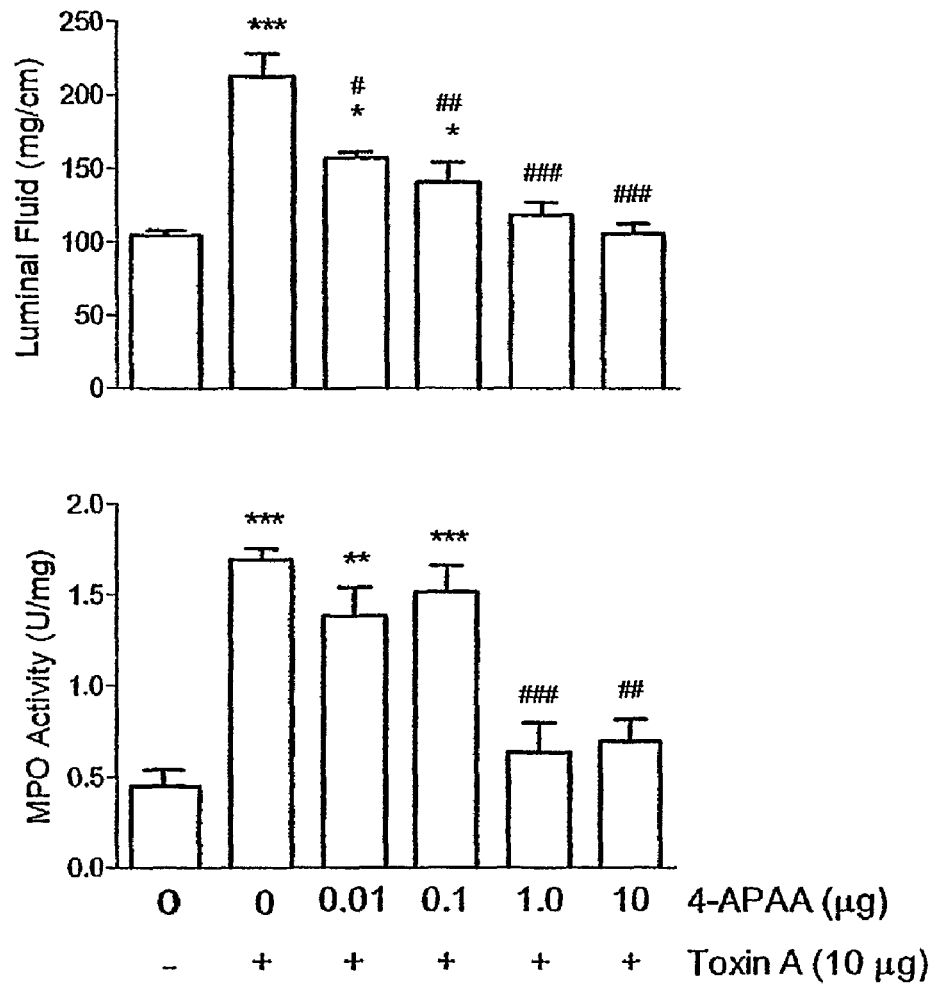
FIG. 18 shows the effects of four doses of 4-APAA on toxin A-induced (10 µg) colonic luminal fluid accumulation and MPO activity.

The effects of treatment with four doses of 4-APAA on toxin A-induced colitis as assessed by luminal fluid accumulation and tissue MPO content are shown in FIG. 18. Toxin A strongly and significantly stimulates luminal fluid accumulation and MPO activity in the rat colon. Acute pretreatment of the rats with all four doses of 4-APAA tested significantly inhibited toxin A-induced luminal fluid accumulation.

Figure 19:
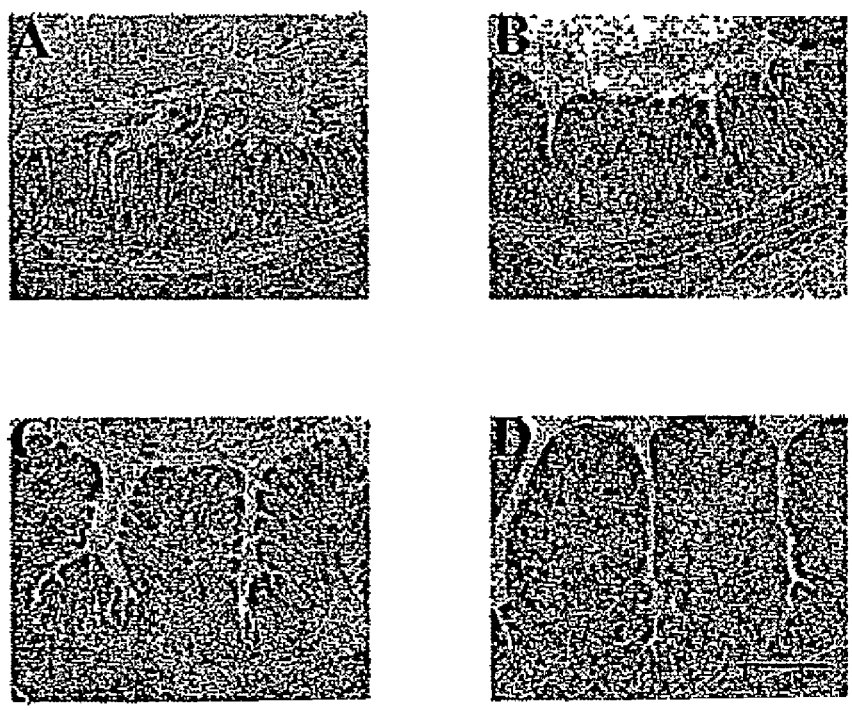
FIGS. 19 A-D show the effects of toxin A on colon histology and inhibition of these effects by treatment with 5-ASA at four doses. H&E-stained sections of rat colon were prepared after the rats were treated for three hours with toxin A (10 µg)

FIG. 19 shows the effects of four doses of 4-APAA on toxin A-induced (10 µg) colonic luminal fluid accumulation and MPO activity. Toxin A significantly stimulated luminal fluid accumulation and MPO activity and toxin A-induced luminal fluid accumulation was significantly inhibited by 4-APAA treatment at all doses tested. Toxin A-induced MPO activity was significantly inhibited by 4-APAA treatment only at the 1.0 and 10 µg 4-APAA doses but not at the 4-APAA doses of 0.01 and 0.1 µg. The values shown are mean+SEM; N=3. *P<0.05 vs. toxin $A^-$/4-APAA 0; P<0.01 vs. toxin $A^-$/4-APAA 0; *P<0.001 vs. toxin $A^-$/4-APAA 0; # P<0.05 vs. toxin $A^+$/4-APAA 0; ## P<0.01 vs. toxin $A^+$/4-APAA 0; ### P<0.001 vs. toxin $A^+$/4-APAA 0.

In contrast, 4-APAA only significantly inhibited toxin A-induced increases in MPO activity at the two highest doses tested, 1.0 and 10 µg. In general, the effects of 4-APAA on MPO activity were more closely correlated with the effects of 4-APAA on colon structure than with the effects of 4-APAA on luminal fluid accumulation.

The effects of acute treatment with 5-ASA at several doses on toxin A-induced structural damage of the colon as assessed by H&E staining of fixed tissue is shown in FIG. 20. It can be seen that 5-ASA at the dose of 0.01 µg did not prevent the loss of mucosal folding, surface ulceration, loss of goblet cells, or infiltration of immune system cells caused by toxin A. There was a correlation between increased protection of the colon and increasing dose of 5-ASA such that 5-ASA at the doses of 0.1 µg partially preserved surface ulceration (FIG. 18B) and mucosal folding was also largely preserved at the 5-ASA dose of 1.0 µg (FIG. 18C). At the 5-ASA dose of 10 µg, the colon was virtually completely protected against the structural damage caused by toxin A (FIG. 18D).

The effects of treatment with four doses of 5-ASA on toxin A-induced colitis as assessed by luminal fluid accumulation and tissue MPO content are shown in FIG. 21. Toxin A strongly and significantly stimulates luminal fluid accumulation and MPO activity in the rat colon. Acute pretreatment of the rats with 5-ASA at the doses of 0.1, 1.0, and 10 µg significantly inhibited toxin A-induced luminal fluid accumulation. In contrast, 5-ASA only significantly inhibited toxin A-induced increases in MPO activity at the two highest doses tested, 1.0 and 10 µg.

To determine if a combination of low doses of 4-APAA and 5-ASA inhibits toxin A colitis in rats, 10 ng (=0.01 µg) each of the two compounds was injected intraluminally into isolated segments of the rat colon 30 minutes prior to toxin A administration. FIG. 20 shows that the combination of 4-APAA and 5-ASA significantly inhibited toxin A-induced structural damage of the rat colon at doses that separately had little effect (cf FIGS. 16 & 18).

The effects of treatment with 10 ng each of 4-APAA, 5-ASA, or both 4-APAA and 5-ASA on toxin A-induced colitis as assessed by luminal fluid accumulation and tissue MPO content are shown in FIG. 22. Toxin A strongly and significantly stimulates luminal fluid accumulation and MPO activity in the rat colon. Acute pretreatment of the rats with 10 ng of 4-APAA or 5-ASA significantly inhibited toxin A-induced luminal fluid accumulation, but the combination of both compounds at the same dose of each inhibited this effect of toxin A even more strongly and this inhibition was significantly different than the inhibition caused by each compound alone. Toxin A-stimulated MPO activity was not significantly inhibited by 4-APAA or 5-ASA at the dose of 10 ng, but the combination of the two compounds at this dose strongly and significantly inhibited this inflammatory effect of the toxin.

The results show that 4-APAA and 5-ASA are approximately equipotent for inhibition of acute toxin A-induced colitis in rats when given alone but when given together appear to inhibit toxin A colitis more than additively. The lowest dose of 4-APAA and 5-ASA tested, 10 ng, did not significantly inhibit toxin A-induced structural damage or MPO activity when the compounds were tested alone, but when the two compounds were given together at this dose, they strongly and highly significantly inhibited these indices of colonic inflammation. While the inventors do not wish to be bound by any particular theory, these observations suggest that 4-APAA and 5-ASA can inhibit intestinal inflammation by different mechanisms. Studies can also be conducted to test lower combination doses of the two compounds to determine the full dose-response curve for these effects in order to ascertain the lowest fully effective dose.

The foregoing examples are illustrative of the present invention, and are not to be construed as limiting thereof. Rather, these embodiments are provided so that this disclosure will be thorough and complete, and will fully convey the scope of the invention to those skilled in the art. Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

The following US patents and patent applications are incorporated herein by reference for their teaching concerning 4-APAA compounds, 5-ASA compounds and 4-APAA compounds azo bonded to 5-ASA compounds: U.S. Pat. No. 6,583,128, Immunoregulatory compounds and derivatives and methods of treating diseases therewith, filed Aug. 29, 2001; U.S. Patent Application No. 60/228,683, Immunoregulatory compounds and derivatives and methods of treating diseases therewith, filed Aug. 29, 2000, and U.S. patent application Ser. No. 10/967,736, Immunoregulatory compounds and derivatives and methods of treating diseases therewith, filed Oct. 18, 2004, and U.S. Patent Application No. 60/555,551, entitled Methods and Compositions employing 4-aminophenylacetic acid compounds, filed Mar. 23, 2004.

We claim:

1. A pharmaceutical composition comprising:
  a first therapeutic agent selected from the group consisting of:
    azo-bonded 4-aminophenylacetic acid (4-APAA) compound;
    non-azo bonded 4-APAA compound; and
    azo-bonded 5-aminosalicylic acid (5-ASA) compound;
    non-azo bonded 5-ASA compound; and
  a second therapeutic agent comprising a
    4-APAA compound azo bonded to a 5-ASA compound.

2. The pharmaceutical composition of claim 1 further comprising another therapeutic agent selected from the group consisting of: steroids, antibiotics, stool softeners, stool hardeners, nutraceuticals, probiotic agents and organisms, and nicotinic agents.

3. The pharmaceutical composition of claim 1 formulated to deliver the first therapeutic agent to the small intestine.

4. The pharmaceutical composition of claim 1 formulated to release the first therapeutic agents along the length of the small intestine and the second therapeutic agent along the length of colon.

5. The pharmaceutical composition of claim 1 formulated to release the second therapeutic agents along the length of the distal portion of the small intestine and the colon.

6. The pharmaceutical composition of claim 1 formulated to release the second therapeutic agents along the length of the colon.

7. The pharmaceutical composition of claim 1 formulated to pass through the stomach and to release the active agent in the intestine.

8. The pharmaceutical composition of claim 1 formulated as a suppository.

9. The pharmaceutical composition of claim 1 formulated for administration as an enema.

10. A pharmaceutical composition comprising at least
  a first and second therapeutic agent, wherein the first therapeutic agent is formulated to release in the stomach or small intestine and selected from the group consisting of
    azo-bonded 4-aminophenylacetic acid (4-APAA compound;
    non-azo bonded 4-APAA compound;
    azo-bonded 5-aminosalicylic acid (5-ASA) compound; and
    non-azo bonded 5-ASA compound; and
  wherein the second therapeutic agent is formulated to release in the distal portion of the small intestine or colon and selected from the group consisting of:
    4-APAA compound azo bonded to a 5-ASA compound; and
    a combination of 4-APAA compound and a 5-ASA compound.

11. The pharmaceutical composition of claim 10 wherein:
  the first therapeutic agent is a 5-ASA compound formulated for release in the stomach and the second therapeutic agent is a 4-APAA compound azo bonded to a 5-ASA compound formulated for release in a distal portion of the small intestine.

12. The pharmaceutical composition of claim 10 wherein:
  the first therapeutic agent is a 5-ASA compound formulated for release in the small intestine and the second therapeutic agent is a 4-APAA compound azo bonded to a 5-ASA compound formulated for release in the colon.

13. A method of treating an inflammatory colon condition comprising administering to a subject a pharmaceutical composition of claim 1 or 10 in an amount sufficient to reduce the inflammatory inflammatory colon condition.

* * * * *